US009713536B2

(12) United States Patent
Foley et al.

(10) Patent No.: US 9,713,536 B2
(45) Date of Patent: Jul. 25, 2017

(54) EXPANDABLE SPINAL IMPLANT AND METHOD OF IMPLANTING SAME

(71) Applicant: Warsaw Orthopedic, Inc., Warsaw, IN (US)

(72) Inventors: Kevin T. Foley, Germantown, TN (US); Roy Lim, Germantown, TN (US); Matthew M. Morrison, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 76 days.

(21) Appl. No.: 14/824,965

(22) Filed: Aug. 12, 2015

(65) Prior Publication Data

US 2017/0042695 A1    Feb. 16, 2017

(51) Int. Cl.
| | | |
|---|---|---|
| A61F 2/44 | (2006.01) | |
| A61F 2/46 | (2006.01) | |
| A61F 2/30 | (2006.01) | |

(52) U.S. Cl.
CPC .......... *A61F 2/4455* (2013.01); *A61F 2/4601* (2013.01); *A61F 2002/30579* (2013.01); *A61F 2002/30622* (2013.01); *A61F 2002/4475* (2013.01)

(58) Field of Classification Search
CPC ........ A61F 2/44; A61F 2/4425; A61F 2/4455; A61F 2002/443; A61B 17/885; A61B 17/8852; A61B 17/8858
See application file for complete search history.

(56) References Cited

U.S. PATENT DOCUMENTS

| | | | | |
|---|---|---|---|---|
| 5,390,683 A | * | 2/1995 | Pisharodi | ................ A61F 2/442 128/898 |
| 5,522,899 A | | 6/1996 | Michelson | |
| 5,693,100 A | * | 12/1997 | Pisharodi | .............. A61F 2/4455 623/17.16 |
| 5,782,832 A | * | 7/1998 | Larsen | ................ A61F 2/30742 623/17.11 |
| 6,126,689 A | * | 10/2000 | Brett | ..................... A61F 2/4455 623/17.15 |
| 6,174,334 B1 | * | 1/2001 | Suddaby | ............... A61F 2/4455 623/17.11 |
| 6,332,895 B1 | * | 12/2001 | Suddaby | ............... A61F 2/4455 623/17.11 |
| 6,454,806 B1 | * | 9/2002 | Cohen | ................... A61F 2/4455 623/17.15 |
| 6,491,724 B1 | | 12/2002 | Ferree | |
| 6,641,614 B1 | * | 11/2003 | Wagner | ................. A61F 2/4455 623/17.15 |
| 6,719,796 B2 | * | 4/2004 | Cohen | ...................... A61F 2/44 623/17.15 |
| 7,070,598 B2 | * | 7/2006 | Lim | ..................... A61B 17/025 606/99 |

(Continued)

*Primary Examiner* — Lynnsy Summitt

(57) ABSTRACT

An expandable spinal implant for insertion in a disc space between two adjacent vertebrae. The expandable spinal implant is moveable from an unexpanded configuration to an expanded configuration. The expandable spinal implant includes a first plate having plastically deformable links, a second plate, two transverse members, and a screw. The screw forces apart the transverse members which causes rotational deformation of the links and separation of the plates.

10 Claims, 34 Drawing Sheets

(56) References Cited

U.S. PATENT DOCUMENTS

| | | | | |
|---|---|---|---|---|
| 7,087,055 | B2* | 8/2006 | Lim | A61B 17/025 606/198 |
| 7,547,325 | B2* | 6/2009 | Biedermann | A61F 2/44 623/17.16 |
| 7,763,028 | B2 | 7/2010 | Lim et al. | |
| 7,824,445 | B2* | 11/2010 | Biro | A61F 2/44 623/17.15 |
| 7,850,733 | B2 | 12/2010 | Baynham et al. | |
| 7,875,078 | B2 | 1/2011 | Wysocki et al. | |
| 7,909,869 | B2 | 3/2011 | Gordon et al. | |
| 8,062,375 | B2 | 11/2011 | Glerum et al. | |
| 8,105,358 | B2 | 1/2012 | Phan | |
| 8,105,382 | B2 | 1/2012 | Olmos et al. | |
| 8,123,810 | B2 | 2/2012 | Gordon et al. | |
| 8,133,232 | B2 | 3/2012 | Levy et al. | |
| 8,187,332 | B2 | 5/2012 | Mcluen | |
| 8,216,278 | B2* | 7/2012 | Gabelberger | A61B 17/7065 606/249 |
| 8,317,798 | B2* | 11/2012 | Lim | A61B 17/025 606/105 |
| 8,382,842 | B2 | 2/2013 | Greenhalgh et al. | |
| 8,394,145 | B2 | 3/2013 | Weiman | |
| 8,398,713 | B2 | 3/2013 | Weiman | |
| 8,403,990 | B2 | 3/2013 | Dryer et al. | |
| 8,435,298 | B2 | 5/2013 | Weiman | |
| 8,491,659 | B2 | 7/2013 | Weiman | |
| 8,518,120 | B2 | 8/2013 | Glerum et al. | |
| 8,523,944 | B2* | 9/2013 | Jimenez | F16C 11/12 623/17.15 |
| 8,556,979 | B2 | 10/2013 | Glerum et al. | |
| 8,568,481 | B2 | 10/2013 | Olmos et al. | |
| 8,628,577 | B1* | 1/2014 | Jimenez | A61F 2/442 623/17.15 |
| 8,628,578 | B2* | 1/2014 | Miller | A61F 2/447 623/17.11 |
| 8,632,595 | B2 | 1/2014 | Weiman | |
| 8,636,746 | B2* | 1/2014 | Jimenez | A61F 2/4611 606/105 |
| 8,663,329 | B2* | 3/2014 | Ernst | A61F 2/442 623/17.15 |
| 8,679,183 | B2 | 3/2014 | Glerum et al. | |
| 8,685,098 | B2 | 4/2014 | Glerum et al. | |
| 8,709,086 | B2 | 4/2014 | Glerum | |
| 8,777,993 | B2* | 7/2014 | Siegal | A61F 2/442 606/246 |
| 8,778,025 | B2 | 7/2014 | Ragab et al. | |
| 8,795,366 | B2 | 8/2014 | Varela | |
| 8,888,853 | B2 | 11/2014 | Glerum et al. | |
| 8,888,854 | B2 | 11/2014 | Glerum et al. | |
| 8,894,711 | B2 | 11/2014 | Varela | |
| 8,894,712 | B2 | 11/2014 | Varela | |
| 8,926,704 | B2 | 1/2015 | Glerum | |
| 8,940,049 | B1* | 1/2015 | Jimenez | A61F 2/447 623/17.15 |
| 8,986,386 | B2* | 3/2015 | Oglaza | A61B 17/7065 606/105 |
| 9,034,041 | B2* | 5/2015 | Wolters | A61B 17/8858 623/17.15 |
| 9,039,771 | B2 | 5/2015 | Glerum et al. | |
| 9,060,876 | B1* | 6/2015 | To | A61F 2/442 |
| 9,119,726 | B2* | 9/2015 | Wei | A61F 2/442 |
| 9,119,730 | B2 | 9/2015 | Glerum et al. | |
| 9,216,098 | B2* | 12/2015 | Trudeau | A61F 2/4657 |
| 9,289,308 | B2* | 3/2016 | Marino | A61F 2/447 |
| 9,320,613 | B2* | 4/2016 | Dmuschewsky | A61F 2/442 |
| 9,421,110 | B2* | 8/2016 | Masson | A61F 2/446 |
| 9,486,328 | B2* | 11/2016 | Jimenez | A61F 2/447 |
| 2004/0133280 | A1* | 7/2004 | Trieu | A61F 2/44 623/17.16 |
| 2008/0114367 | A1* | 5/2008 | Meyer | A61B 17/025 606/90 |
| 2008/0183204 | A1* | 7/2008 | Greenhalgh | A61B 17/8858 606/198 |
| 2008/0281346 | A1* | 11/2008 | Greenhalgh | A61B 17/8858 606/191 |
| 2009/0299478 | A1* | 12/2009 | Carls | A61F 2/4425 623/17.16 |
| 2010/0082109 | A1* | 4/2010 | Greenhalgh | A61F 2/447 623/17.15 |
| 2011/0054621 | A1 | 3/2011 | Lim | |
| 2011/0172774 | A1 | 7/2011 | Varela | |
| 2012/0004732 | A1* | 1/2012 | Goel | A61F 2/4455 623/17.16 |
| 2012/0035729 | A1 | 2/2012 | Glerum et al. | |
| 2012/0109319 | A1 | 5/2012 | Perisic | |
| 2012/0150304 | A1 | 6/2012 | Glerum et al. | |
| 2012/0150305 | A1 | 6/2012 | Glerum et al. | |
| 2012/0158146 | A1 | 6/2012 | Glerum et al. | |
| 2012/0158147 | A1 | 6/2012 | Glerum et al. | |
| 2012/0158148 | A1 | 6/2012 | Glerum et al. | |
| 2013/0079882 | A1* | 3/2013 | Wolfe | A61F 2/4455 623/17.16 |
| 2013/0144388 | A1 | 6/2013 | Emery et al. | |
| 2013/0158664 | A1 | 6/2013 | Palmatier et al. | |
| 2013/0190876 | A1* | 7/2013 | Drochner | A61F 2/442 623/17.16 |
| 2014/0121774 | A1 | 5/2014 | Glerum et al. | |
| 2014/0180419 | A1* | 6/2014 | Dmuschewsky | A61F 2/442 623/17.16 |
| 2014/0194992 | A1* | 7/2014 | Medina | A61F 2/4611 623/17.16 |
| 2014/0236296 | A1* | 8/2014 | Wagner | A61F 2/447 623/17.15 |
| 2014/0257486 | A1* | 9/2014 | Alheidt | A61F 2/447 623/17.15 |
| 2014/0257489 | A1* | 9/2014 | Warren | A61B 17/1671 623/17.16 |
| 2014/0277139 | A1* | 9/2014 | Vrionis | A61B 17/70 606/246 |
| 2014/0324171 | A1 | 10/2014 | Glerum et al. | |
| 2015/0100128 | A1* | 4/2015 | Glerum | A61F 2/447 623/17.16 |
| 2016/0166396 | A1* | 6/2016 | McClintock | A61F 2/30771 623/17.16 |
| 2016/0250034 | A1* | 9/2016 | Loebl | A61F 2/44 |
| 2016/0324654 | A1* | 11/2016 | Loebl | A61F 2/4455 |

\* cited by examiner

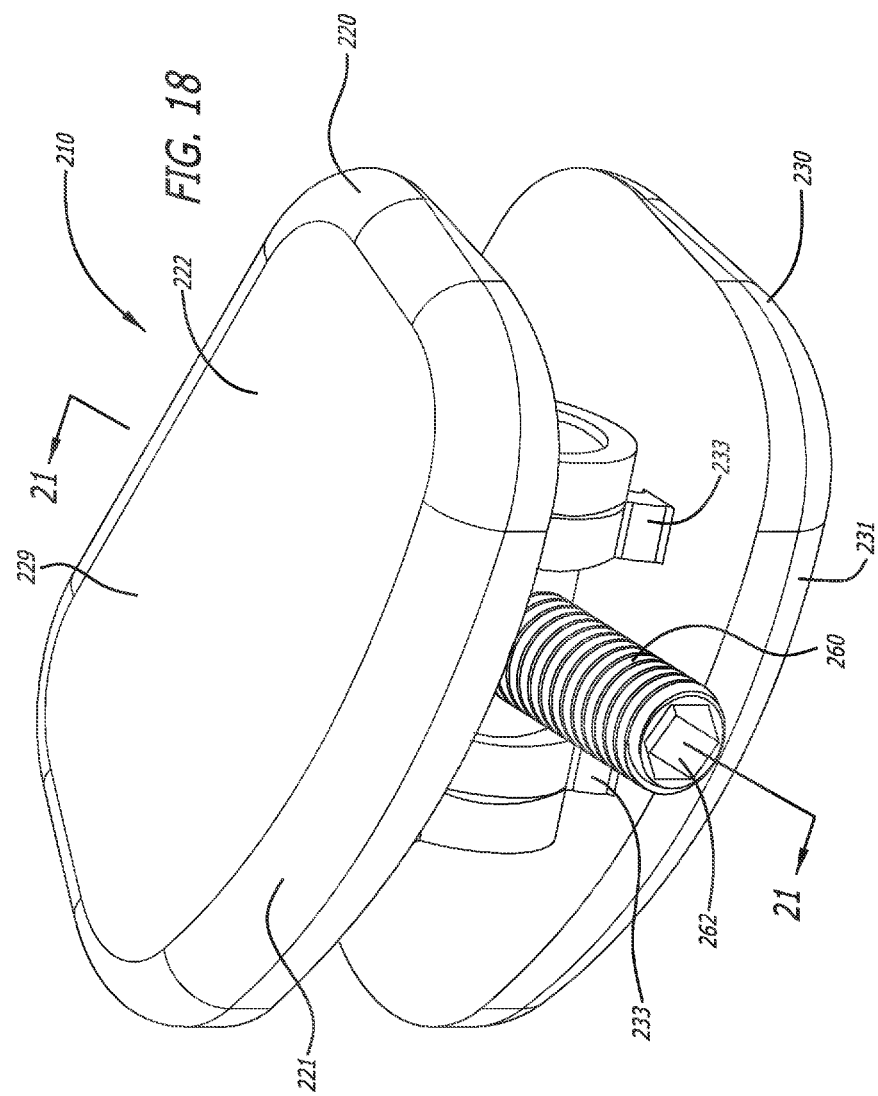

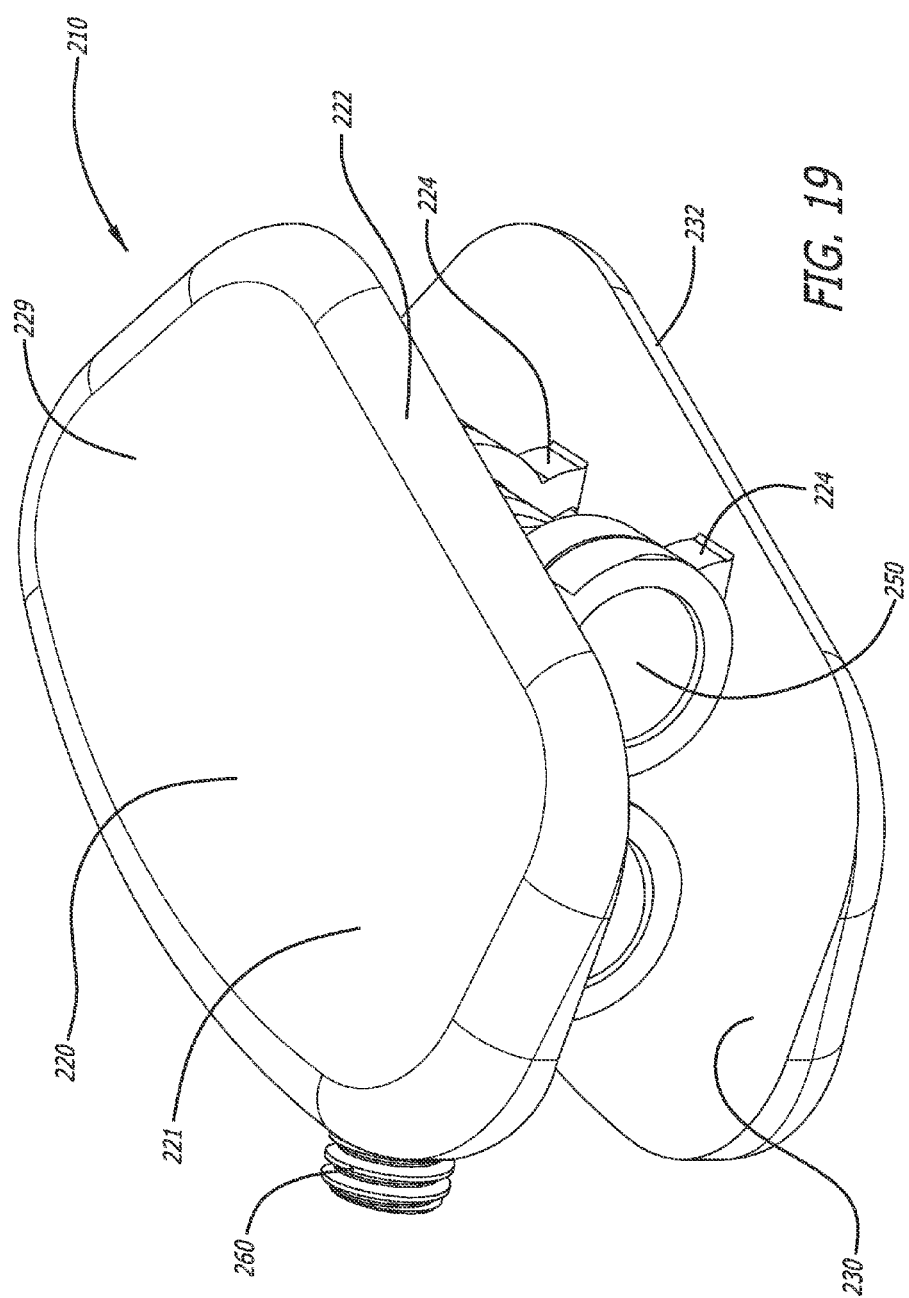

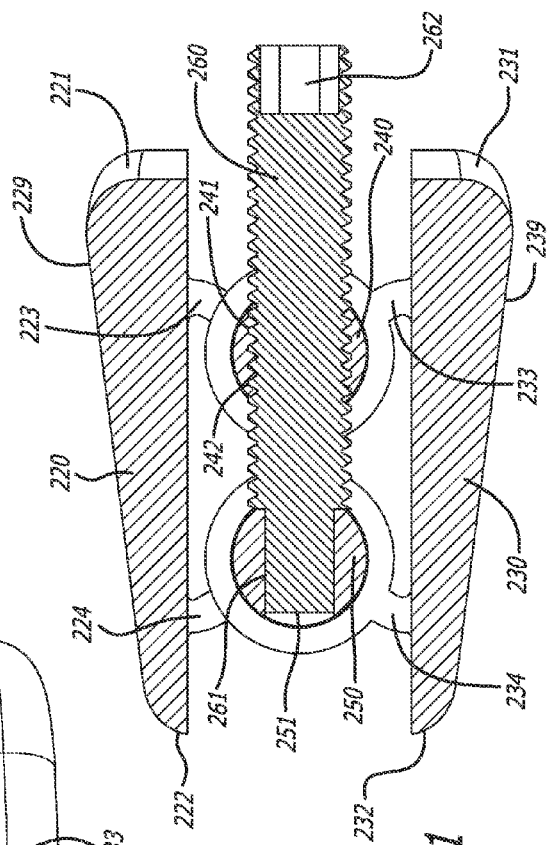
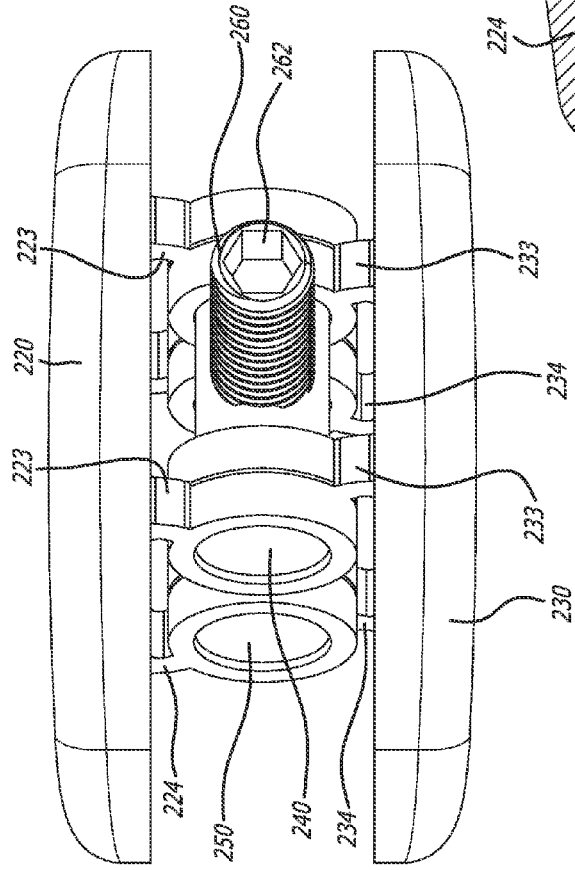

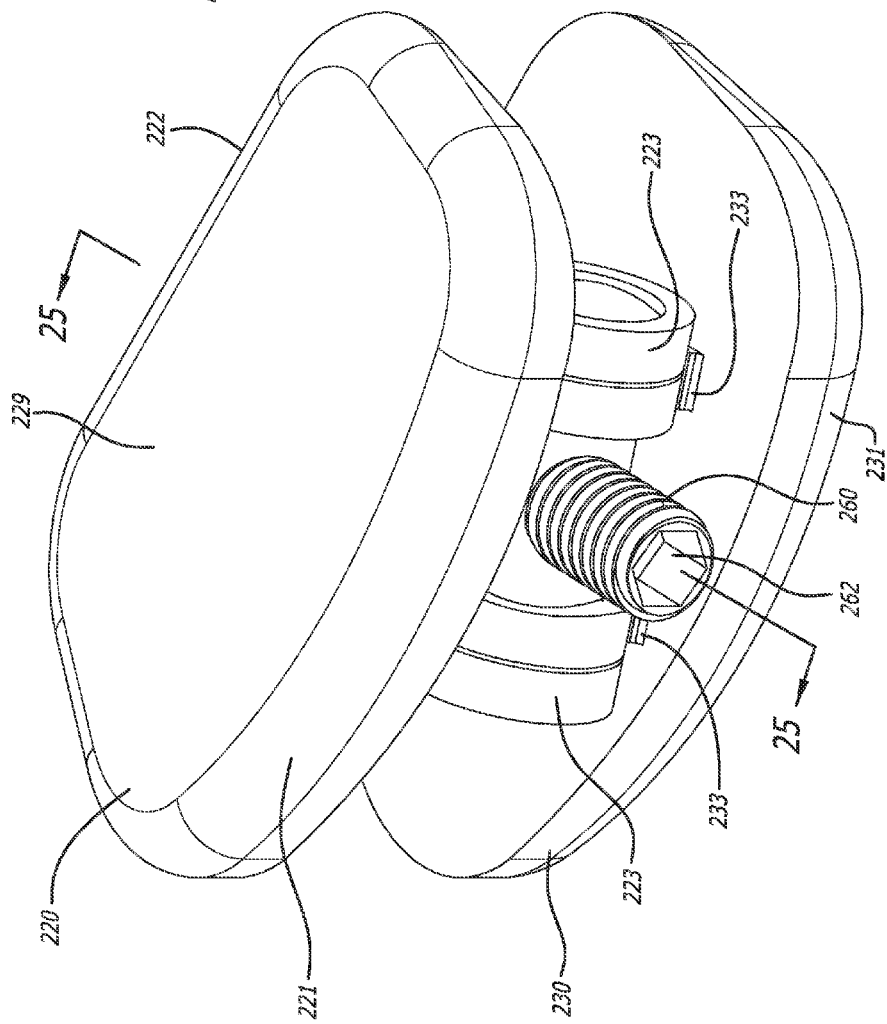

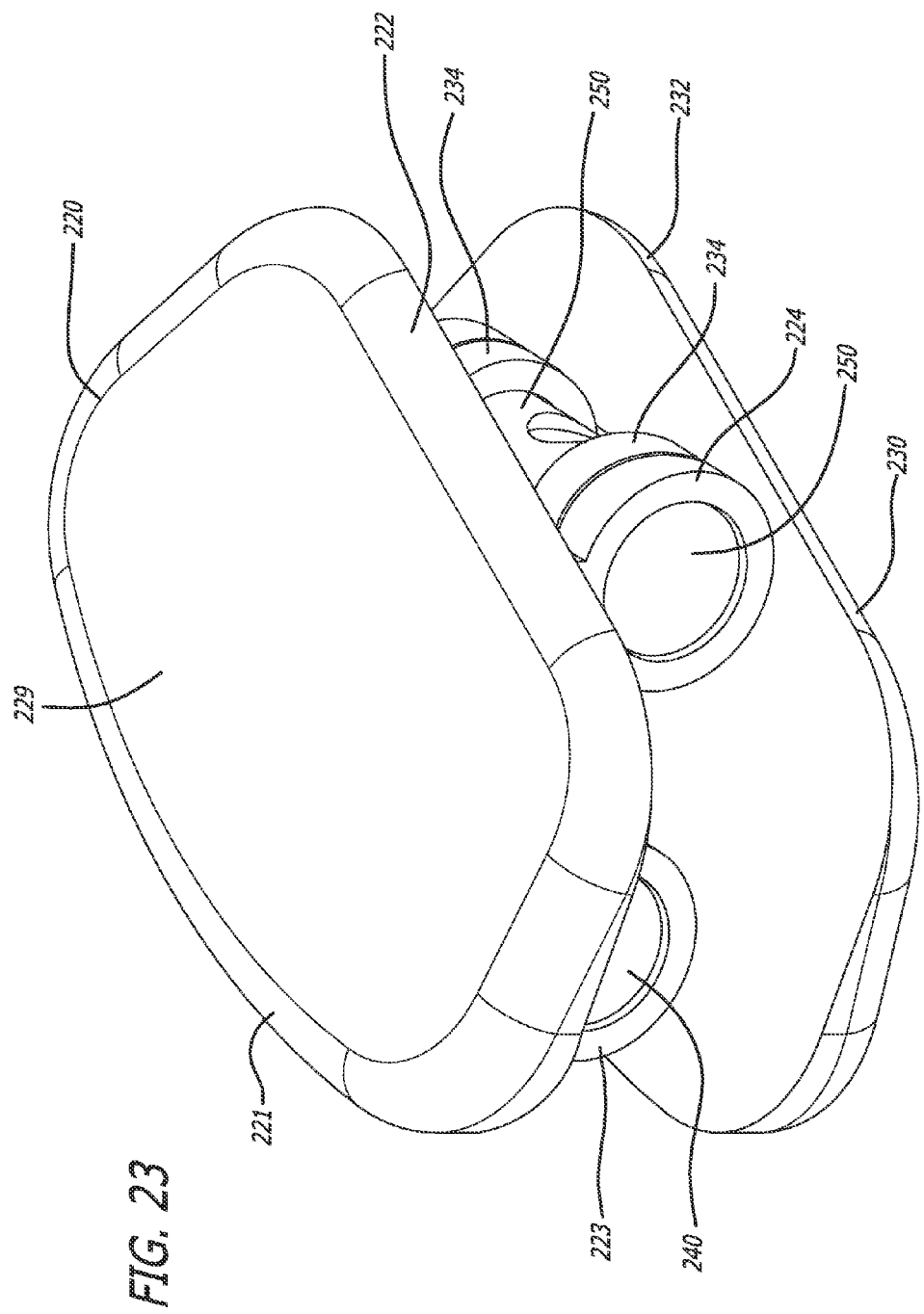

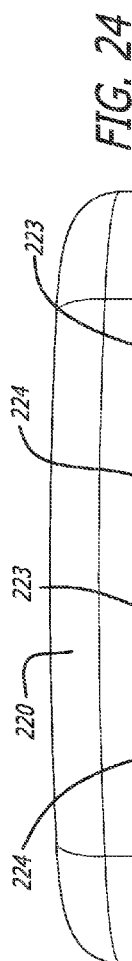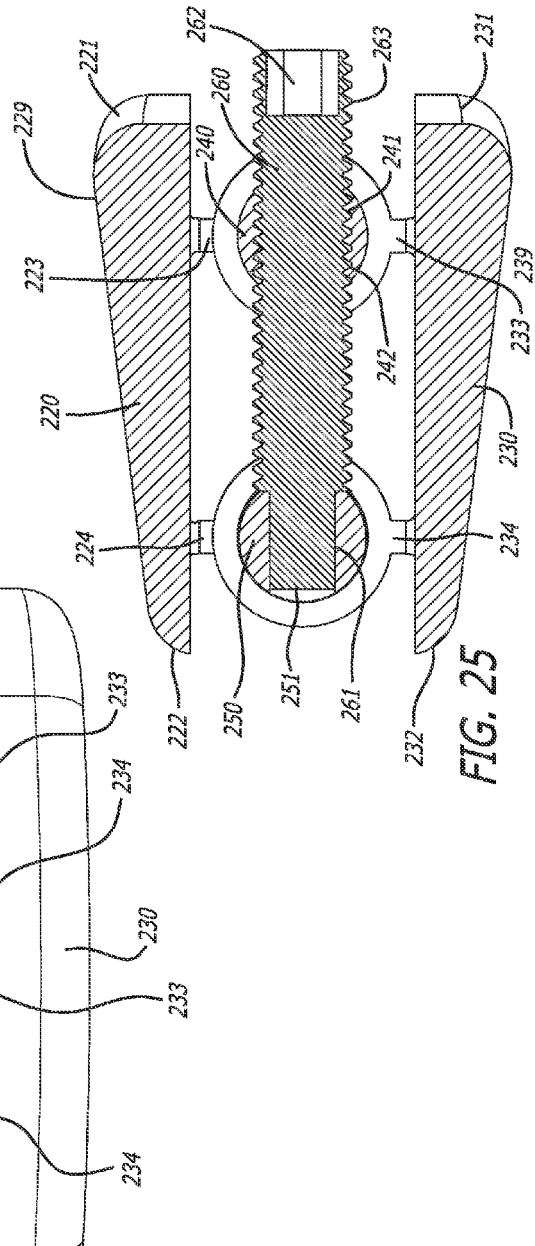

EXPANDABLE SPINAL IMPLANT AND METHOD OF IMPLANTING SAME

BACKGROUND OF THE INVENTION

The present invention relates to an expandable spinal implant for use in spinal surgery. More particularly, the present invention relates to a plastically deformable expandable spinal implant for implantation into a disc space between two adjacent vertebrae, movable from an unexpanded configuration to an expanded configuration. More specifically, the present invention relates to a plastically deformable expandable spinal implant that includes two plates, wherein at least one of the two plates includes at least one link or pair of links rotationally attached to a transverse member located between the plates, and advancement of a screw causes translation of the transverse member, rotation of the at least one link or pair of links, and separation of the plates.

DESCRIPTION OF THE RELATED ART

Expandable spinal implants are known in the art. Such expandable spinal implants can be configured to ultimately have lordotic, tapered configurations to assist in the restoration or enhancement of spinal lordosis. The expandability of such implants allows placement thereof into a corresponding surgically-enhanced disc space between two adjacent vertebrae through a relatively small surgical opening in a patient's body. Thereafter, expansion of the implants provides the advantage of increasing the heights thereof within the disc space to assist in the restoration or enhancement of spinal lordosis.

The related art implants are typically expanded by translating a wedge along a ramp or by rotation of a generally rectangular shaped blocker.

SUMMARY OF THE INVENTION

In accordance with the invention, a plastically deformable expandable spinal implant is configured to be inserted into a disc space between two adjacent vertebrae.

The expandable spinal implant includes a first plate having a proximal end and an opposite distal end, a bone contacting surface configured to contact one of the two adjacent vertebrae, a mid-longitudinal axis extending between the proximal and distal ends, and first and second links or pairs of links extending away from the bone contacting surface at an acute angle to the mid-longitudinal axis.

The expandable spinal implant includes a second plate having a proximal end and an opposite distal end, a bone contacting surface configured to contact the other of the two adjacent vertebrae, a mid-longitudinal axis extending between the proximal and distal ends, and third and fourth links or pairs of links extending away from the bone contacting surface at an acute angle to the mid-longitudinal axis.

The expandable spinal implant further includes a first transverse member located between the bone contacting surfaces of the first and second plates and being rotationally attached to the first and third links or pairs of links, the first transverse member including a threaded opening that extends therethrough.

The expandable spinal implant further includes a second transverse member located between the bone contacting surfaces of the first and second plates and being rotationally attached to the second and fourth links or pairs of links, the second transverse member including an opening that extends at least partially therein.

The expandable spinal implant further includes a screw having a threaded section sized and shaped to be threaded through the opening in the first transverse member, the screw including a leading end sized and shaped to fit within the opening in the second transverse member.

The expandable spinal implant is configured such that advancing the screw through the opening in the first transverse member causes separation of the transverse members, which preferably causes plastic deformation of the links via rotation thereof, resulting in an increase in the distance between the bone contacting surfaces of the first and second plates. Preferably, the first and second plates will expand to a position defining a right angle between the plates. Angles of less than 90°, however, also are possible.

In accordance with yet another aspect of the present invention, a method of implanting an expandable spinal implant into a disc space between two adjacent vertebrae is provided. The method includes utilizing the expandable spinal implant defining a longitudinal axis, the expandable spinal implant including: a first plate having a bone contacting surface and one of first and second links and first and second pairs of links extending away from the bone contacting surface; a second plate having a bone contacting surface, and one of third and fourth links and third and fourth pairs of links extending away from the bone contacting surface; a first transverse member rotationally attached to the first and third links or pairs of links, transverse to the longitudinal axis; a second transverse member rotationally attached to the second and fourth links or pairs of links transverse to the longitudinal axis, at least one of the first transverse member and the second transverse member including an opening extending at least partially therein, the opening being coaxial with the longitudinal axis; and a screw threaded through the threaded opening, the screw including a non-threaded leading end inserted into the opening in the at least one of the first transverse member and the second transverse member. The method further includes inserting the expandable spinal implant into the disc space and rotating the screw, wherein rotating the screw causes the transverse members to separate, which causes rotation of the four links or pairs of links, and separation of the first and second plates. Rotation of the links or pairs of links, and separation of the first and second plates can be a result of plastic deformation of the links or pairs of links. Alternately, hinges can be provided on a side of the implant or on an end of the implant, or a combination of hinges and plastic deformation can be employed.

The present invention may be utilized in a variety of different spinal surgical procedures including but not limited to transforaminal lumbar interbody fusion (TLIF), posterior lumbar interbody fusion (PLIF), direct lateral interbody fusion (DLIF), anterior lumbar interbody fusion (ALIF), or oblique lumbar interbody fusion (OLIF). The expandable implants may vary in length, height, width, and angle between the bone contacting surfaces depending on which procedure the expandable spinal implant is being used for, as well as the size of the patient's anatomical structures.

BRIEF DESCRIPTION OF THE DRAWINGS

The accompanying drawings, which are incorporated in and constitute a part of the specification, illustrate preferred embodiments of the invention and, together with the description, serve to explain the objects, advantages, and principles of the invention. In the drawings:

FIG. 18 is a rear perspective view of another embodiment of an expandable spinal implant in accordance with the present invention in an unexpanded configuration;

FIG. 19 is a front perspective view of the expandable spinal implant of FIG. 18 in the unexpanded configuration;

FIG. 20 is a side elevational view of the expandable spinal implant of FIGS. 18-20 in the unexpanded configuration;

FIG. 21 is a cross-sectional view along Line 21-21 of FIG. 18 showing the expandable spinal implant of FIGS. 18-20 in the unexpanded configuration;

FIG. 22 is a rear perspective view of the expandable spinal implant of FIGS. 18-21 in an expanded configuration;

FIG. 23 is a front perspective view of the expandable spinal implant of FIGS. 18-22 in the expanded configuration;

FIG. 24 is a side elevational view of the expandable spinal implant of FIGS. 18-23 in the expanded configuration;

FIG. 25 is a cross-sectional view along Line 25-25 of FIG. 22 showing the expandable spinal implant of FIGS. 18-24 in the expanded configuration;

DETAILED DESCRIPTION OF THE PREFERRED EMBODIMENT

Figure 1:
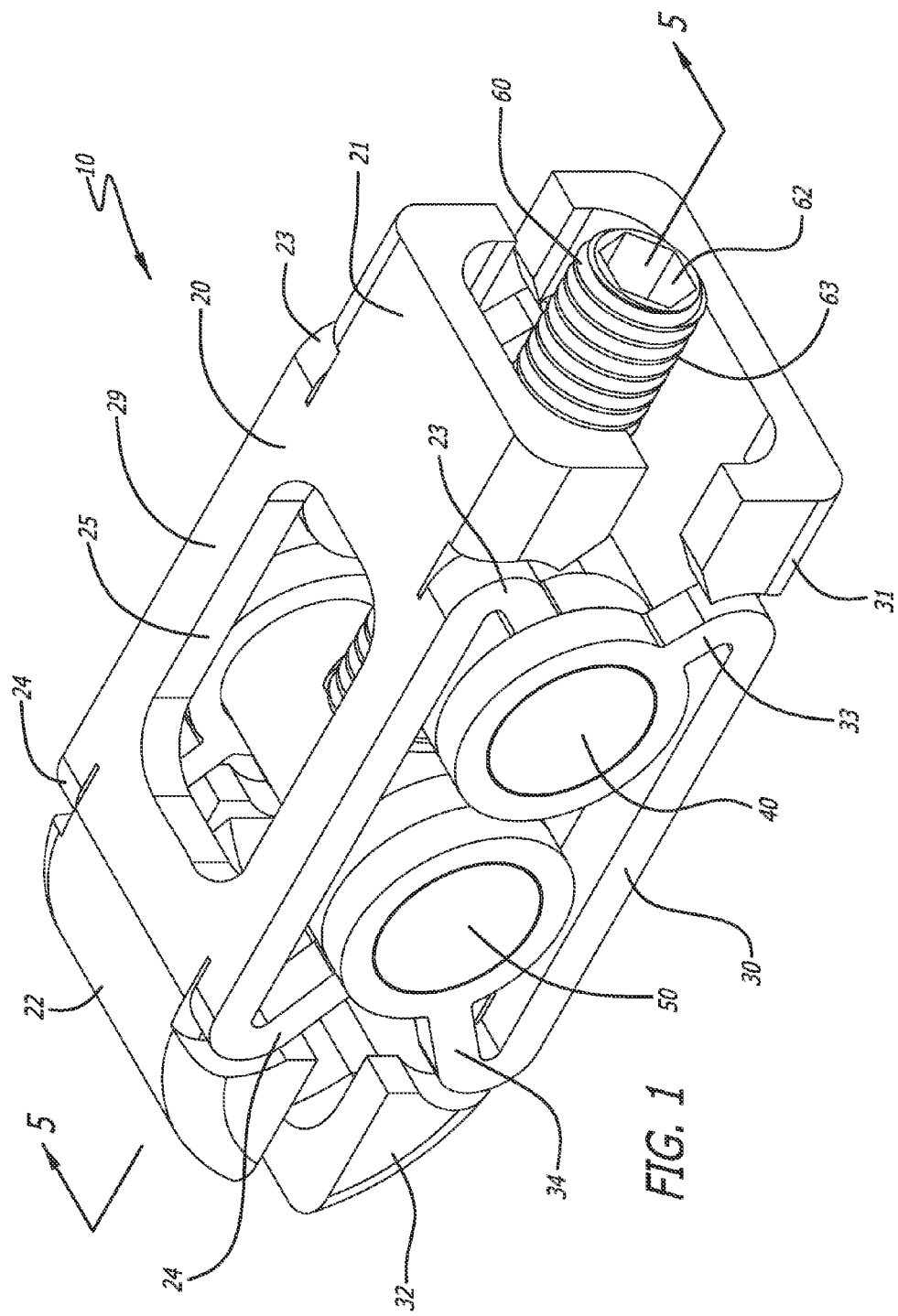
FIG. 1 is a rear perspective view of an expandable spinal implant in accordance with the present invention in an unexpanded configuration.
Figure 2:
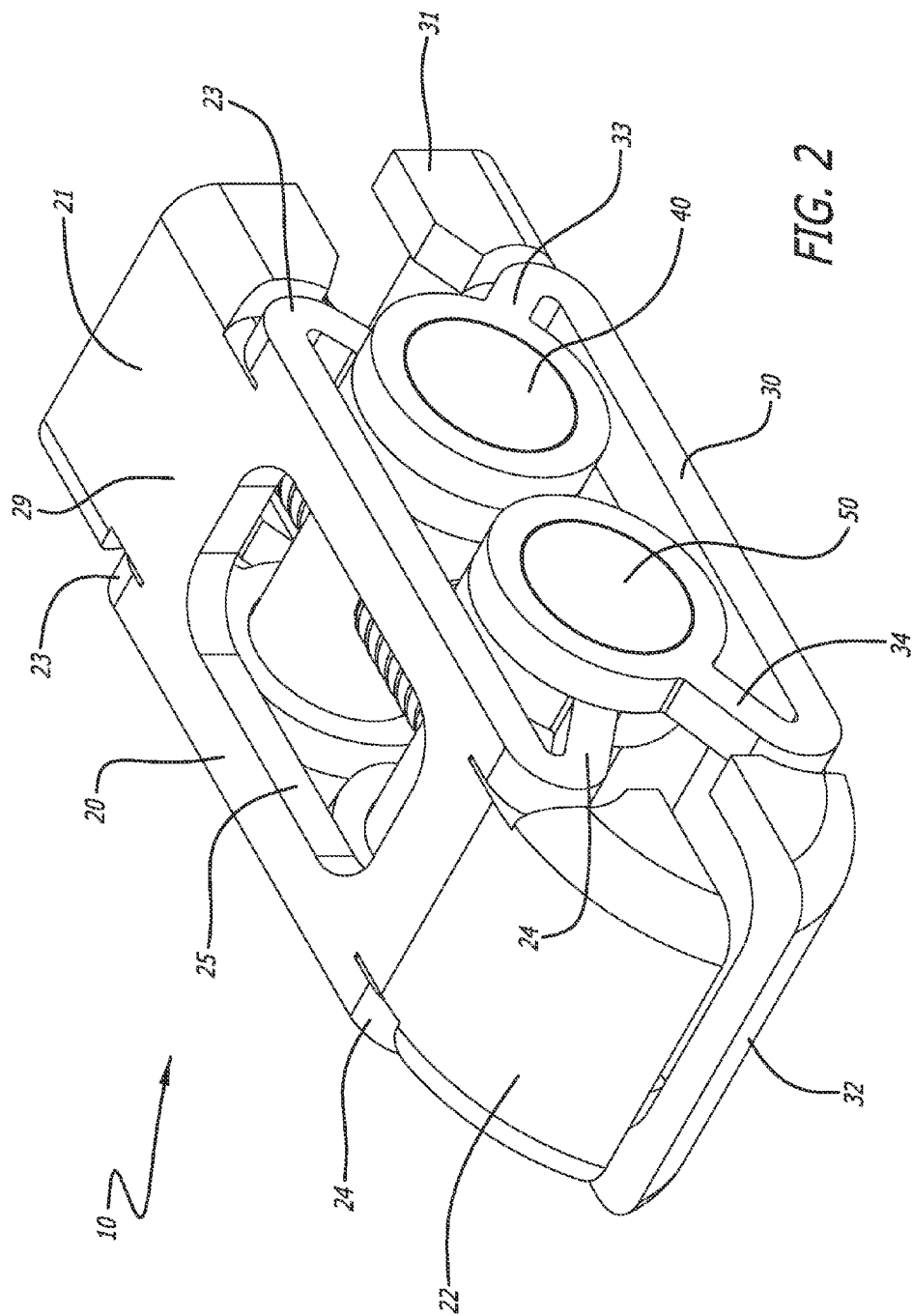
FIG. 2 is a front perspective view of the expandable spinal implant of FIG. 1 in the unexpanded configuration.
Figure 3:
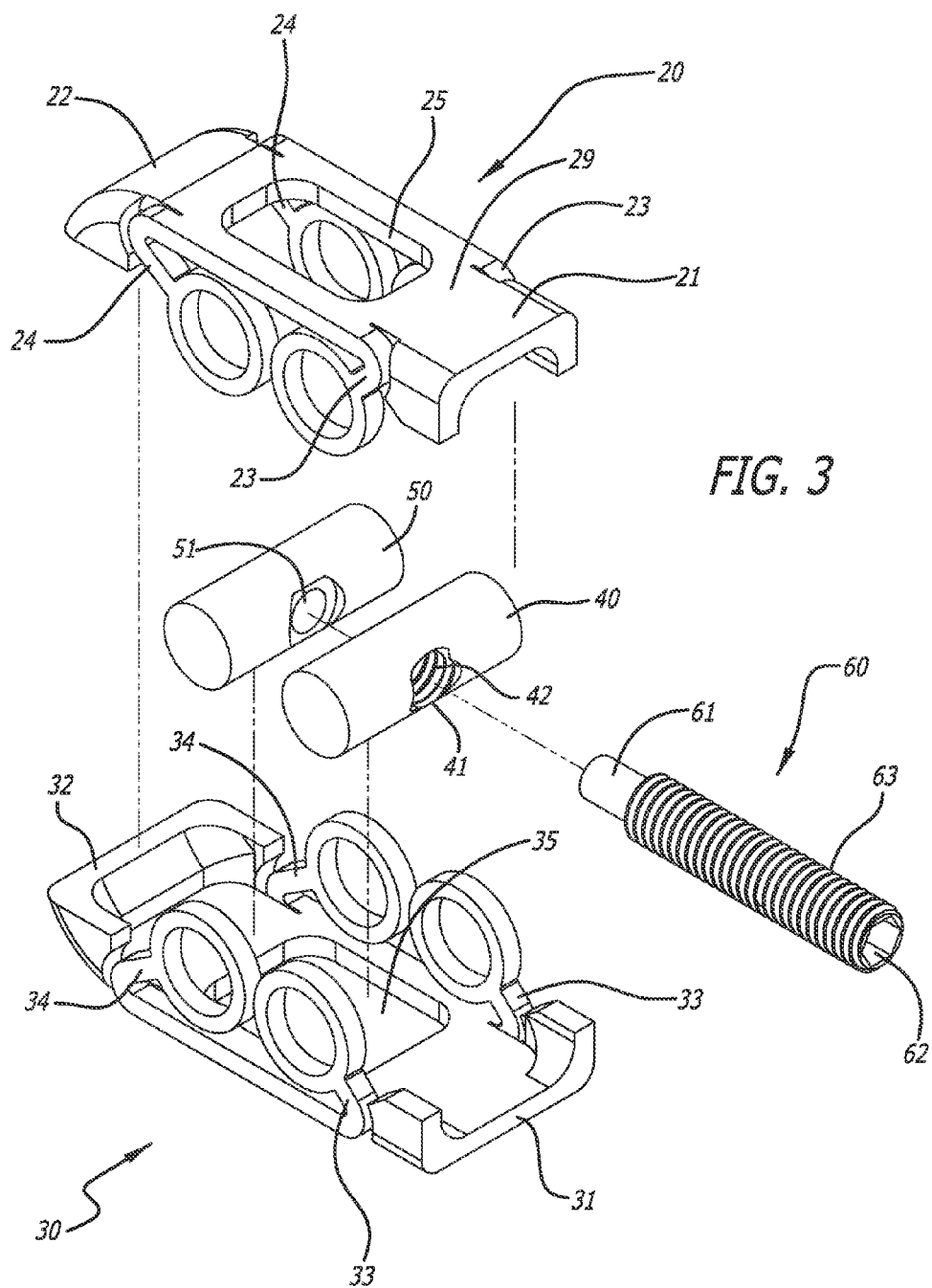
FIG. 3 is an exploded rear perspective view of the expandable spinal implant of FIGS. 1 and 2.
Figure 4:
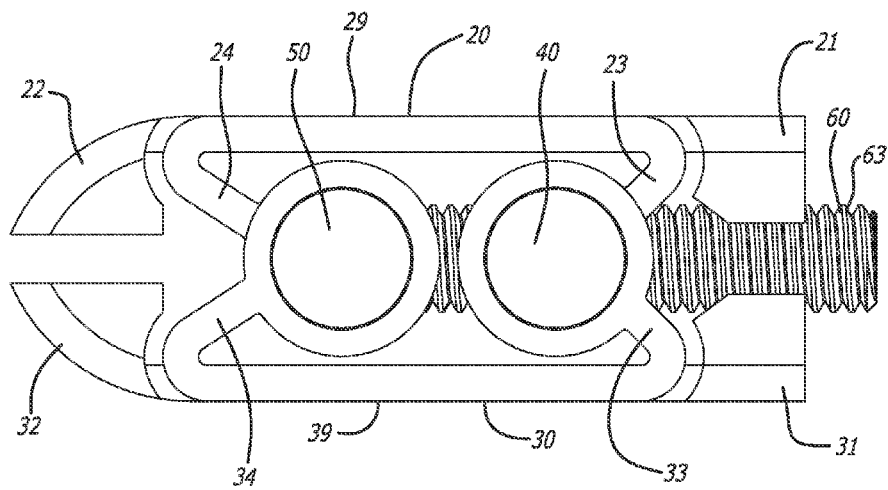
FIG. 4 is a side elevational view of the expandable spinal implant of FIGS. 1-3 in the unexpanded configuration.
Figure 5:
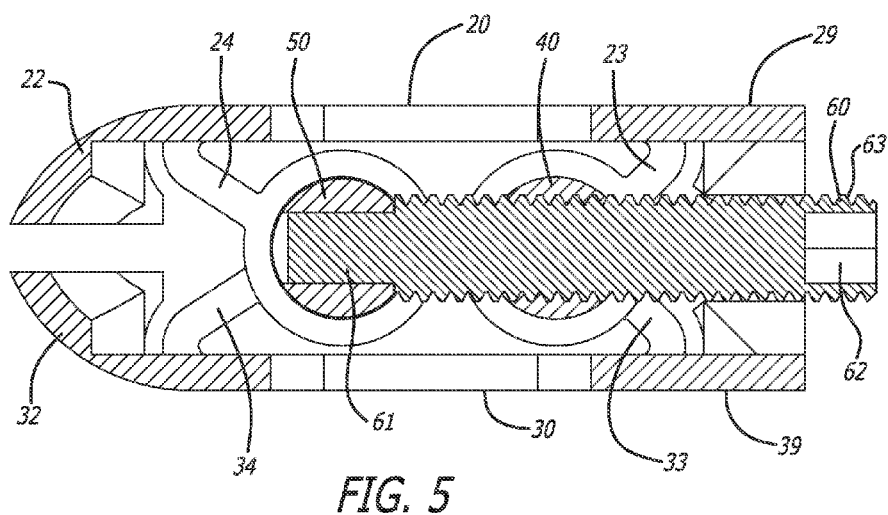
FIG. 5 is a cross sectional view along Line 5-5 of FIG. 1 of the expandable spinal implant of FIGS. 1-4 in the unexpanded configuration.
Figure 6:
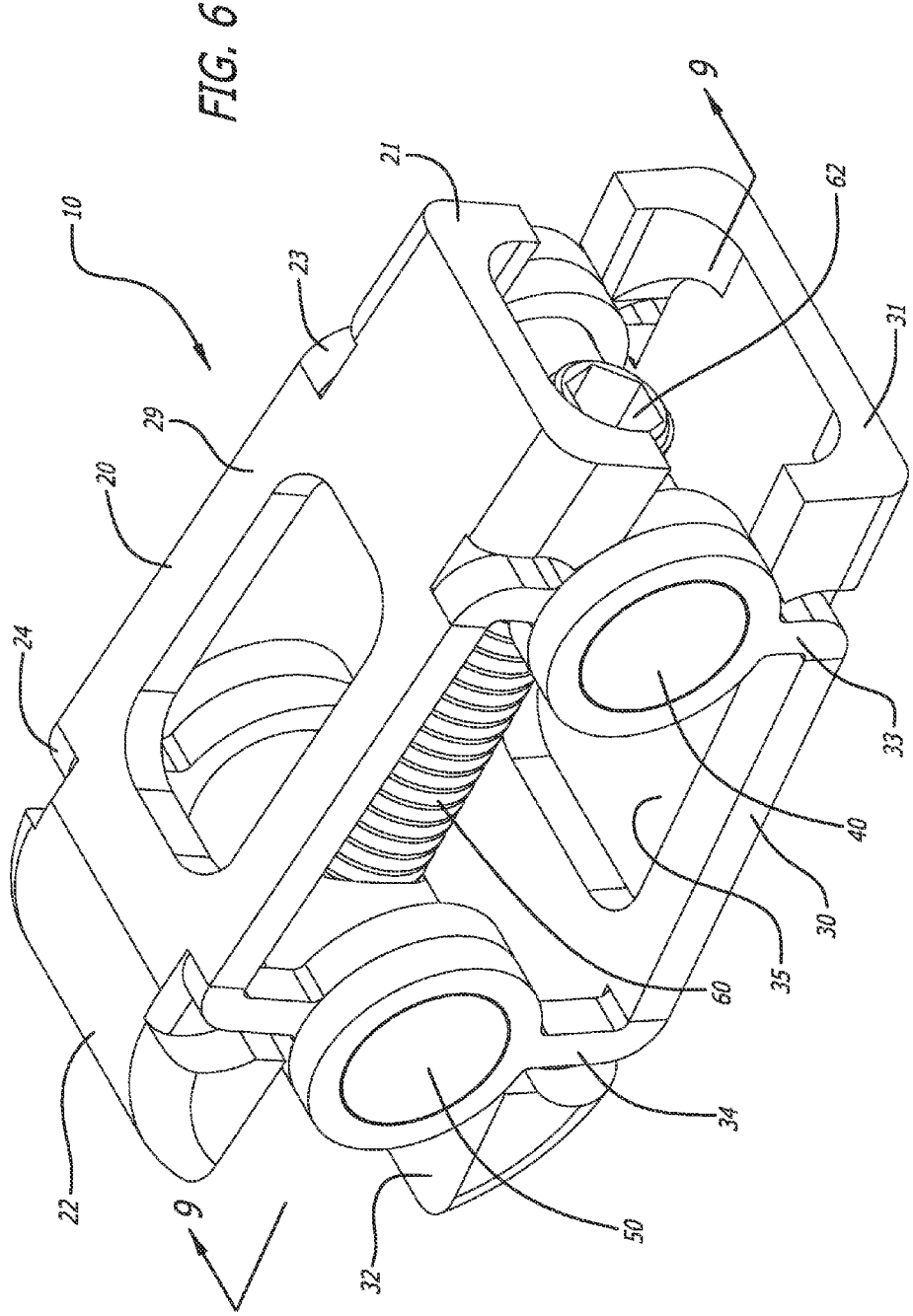
FIG. 6 is a rear perspective view of the expandable spinal implant of FIGS. 1-5 in the expanded configuration.
Figure 7:
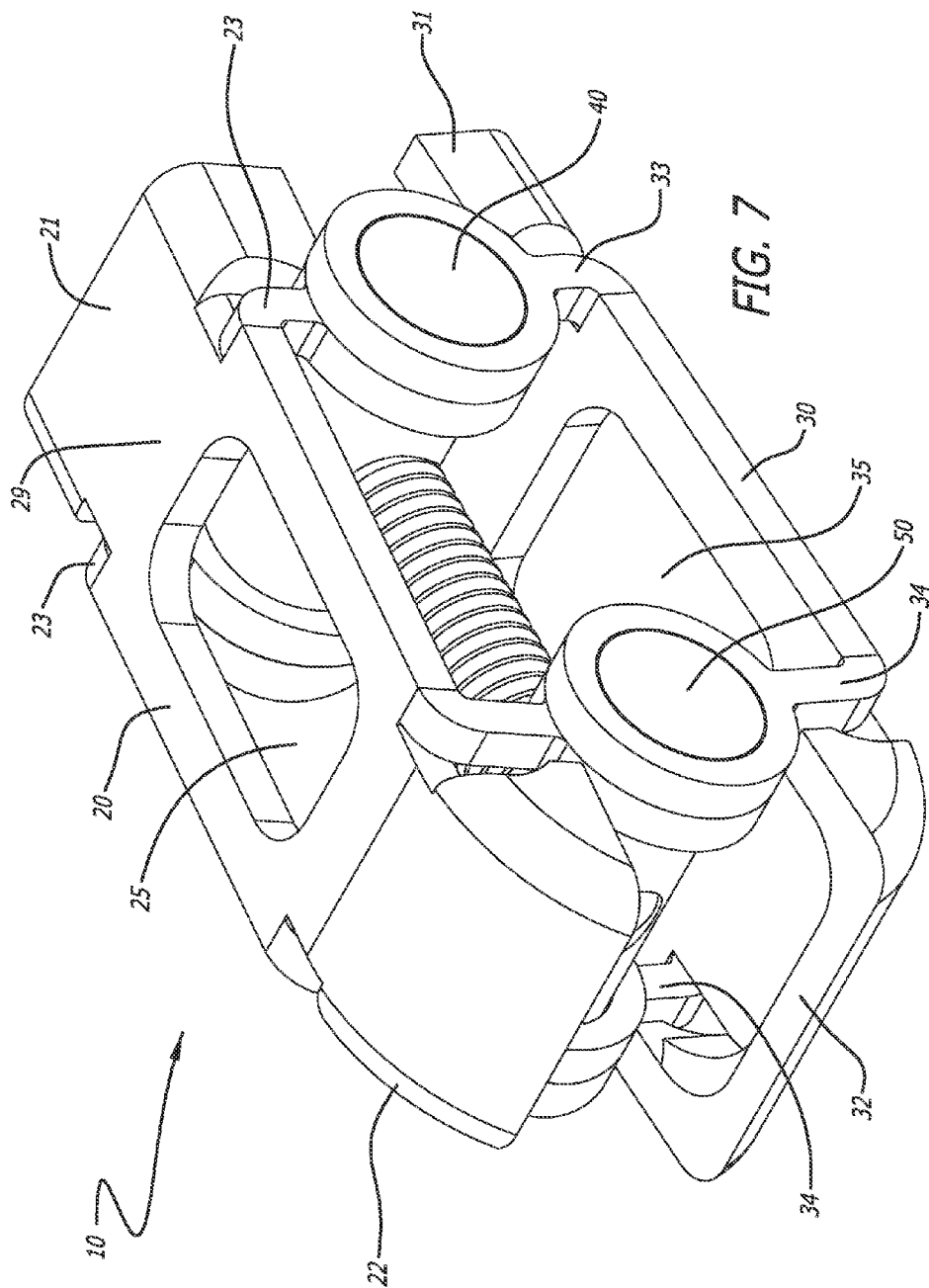
FIG. 7 is a front perspective view of a leading end of the expandable implant of FIGS. 1-6 in the expanded configuration.
Figure 8:
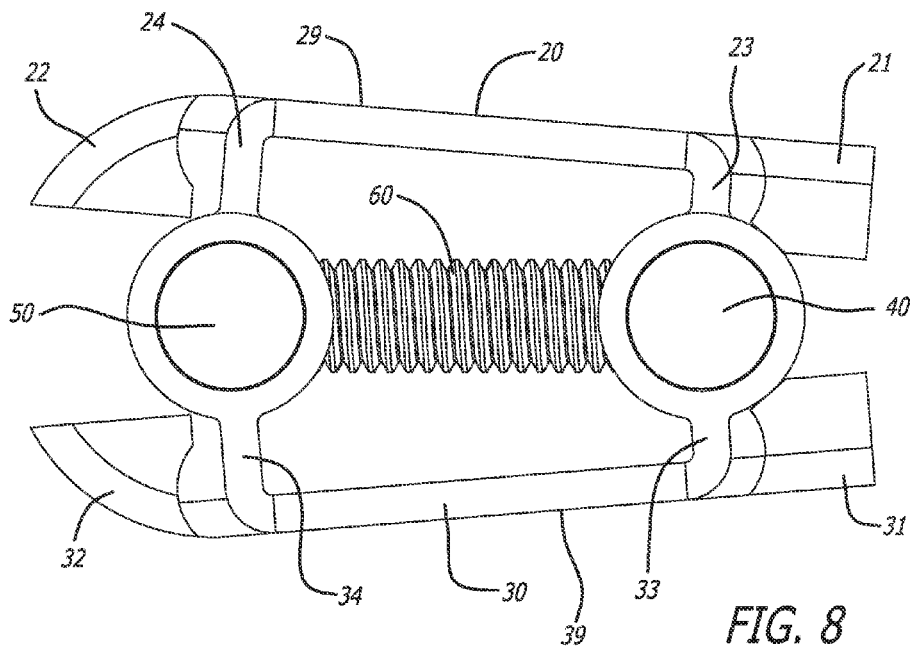
FIG. 8 is a side elevational view of the expandable spinal implant of FIGS. 1-7 in the expanded configuration.
Figure 9:
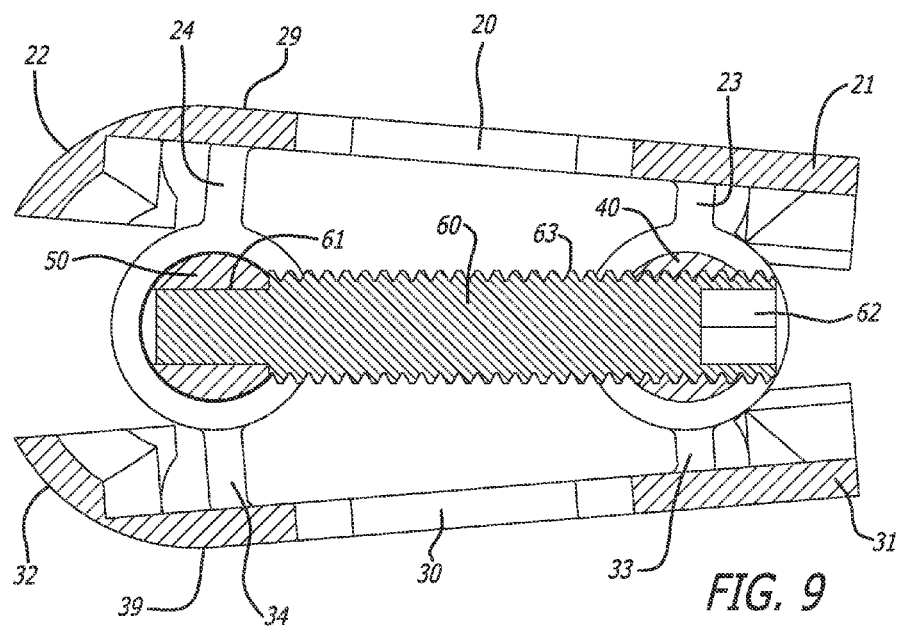
FIG. 9 is a cross-sectional view along Line 9-9 of FIG. 6 of the expandable spinal implant of FIGS. 1-8 in the expanded configuration.
Figure 10:
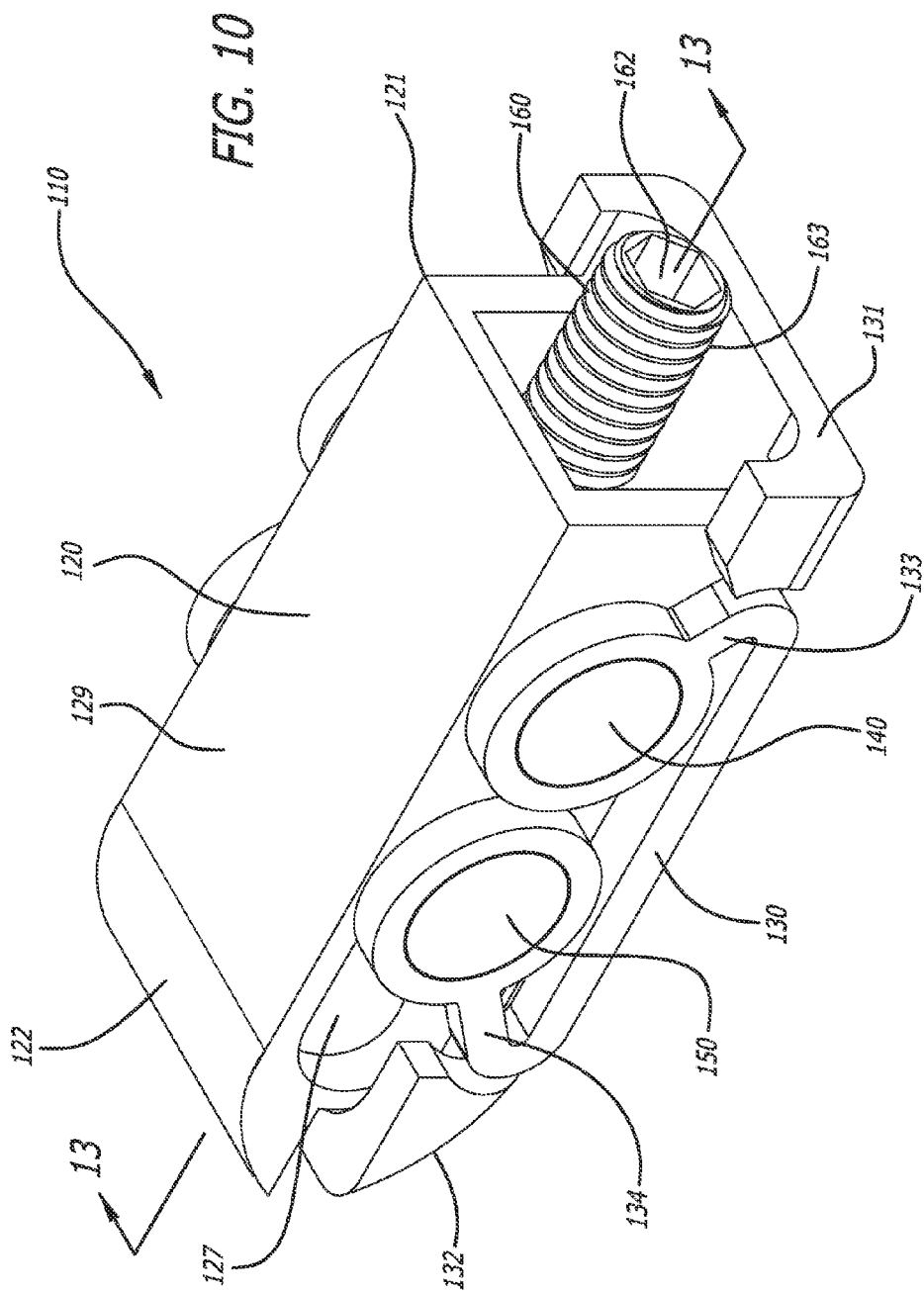
FIG. 10 is a rear perspective view of another embodiment of an expandable spinal implant in accordance with the present invention in an unexpanded configuration.
Figure 11:
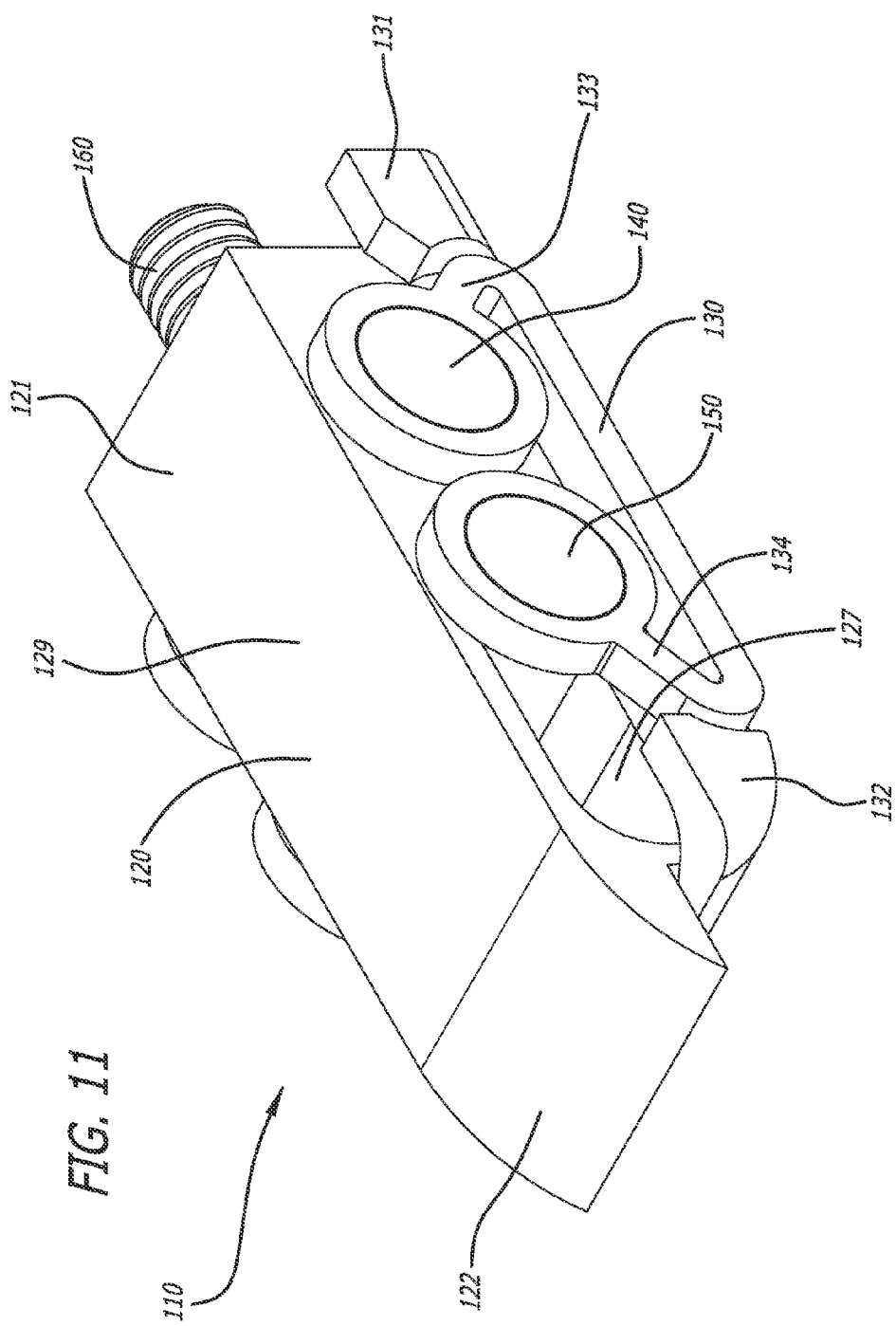
FIG. 11 is a front perspective view of the expandable spinal implant of FIG. 10 in the unexpanded configuration.
Figure 12:
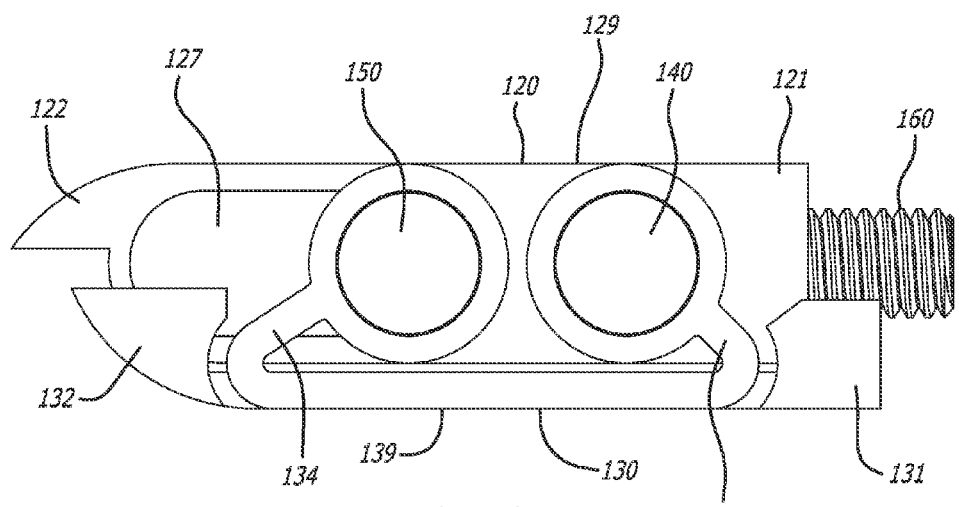
FIG. 12 is a side elevational view of the expandable spinal implant of FIGS. 10 and 11 in the unexpanded configuration.
Figure 13:
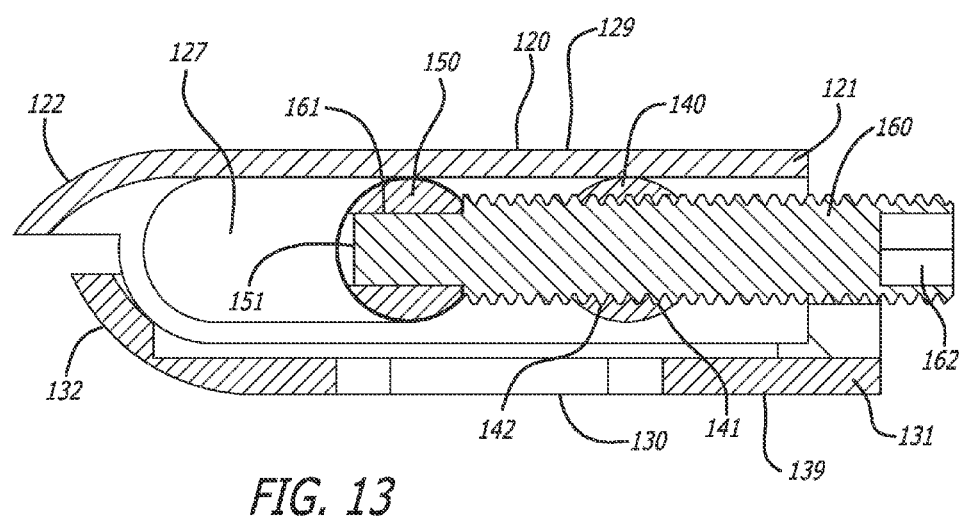
FIG. 13 is a cross-sectional view along Line 13-13 of FIG. 10 showing the spinal implant of FIGS. 10-12 in the unexpanded configuration.
Figure 14:
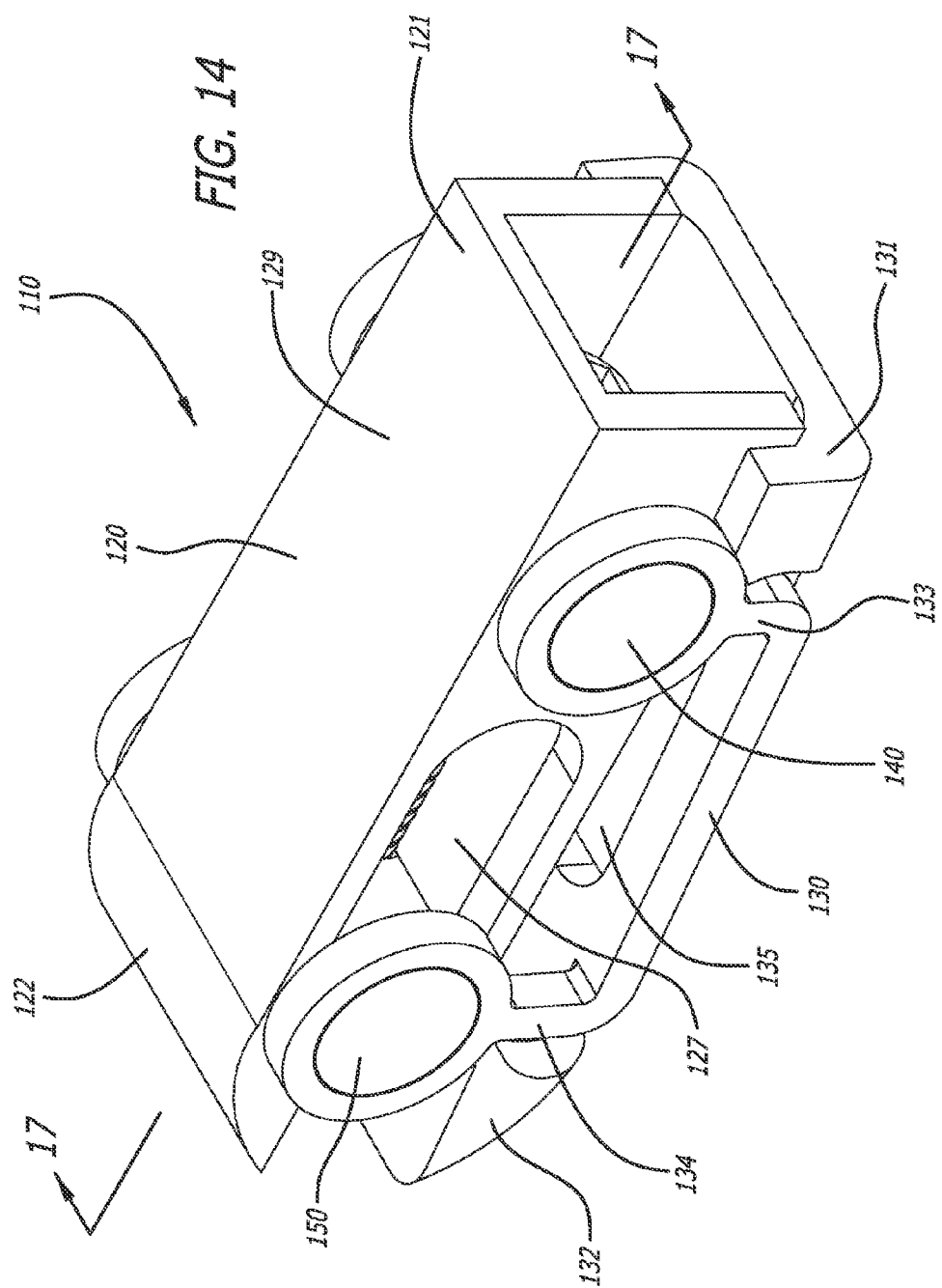
FIG. 14 is a rear perspective view of the expandable spinal implant of FIGS. 10-13 in an expanded configuration.
Figure 15:
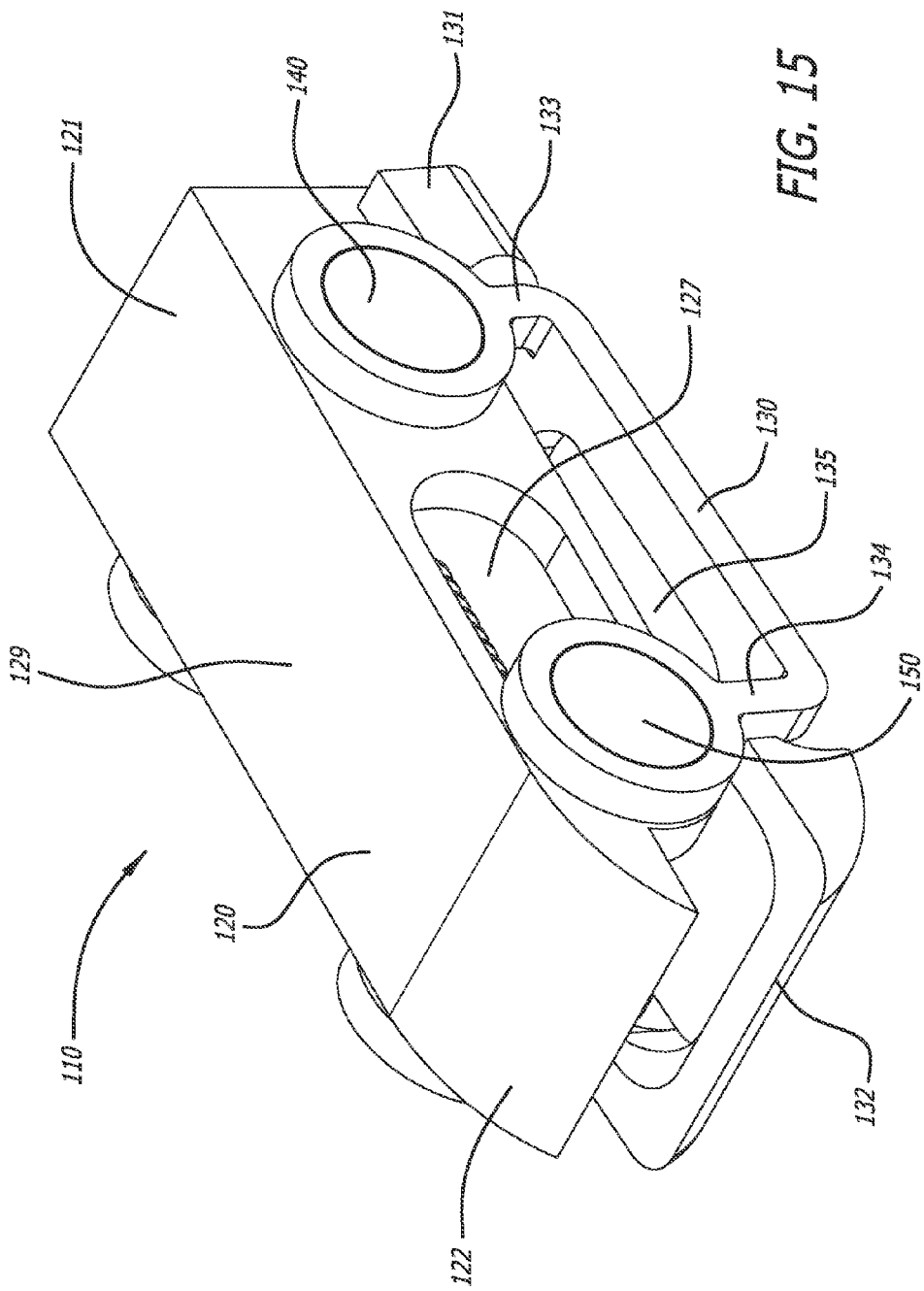
FIG. 15 is a front perspective view of the expandable spinal implant of FIGS. 10-14 in the expanded configuration.
Figure 16:
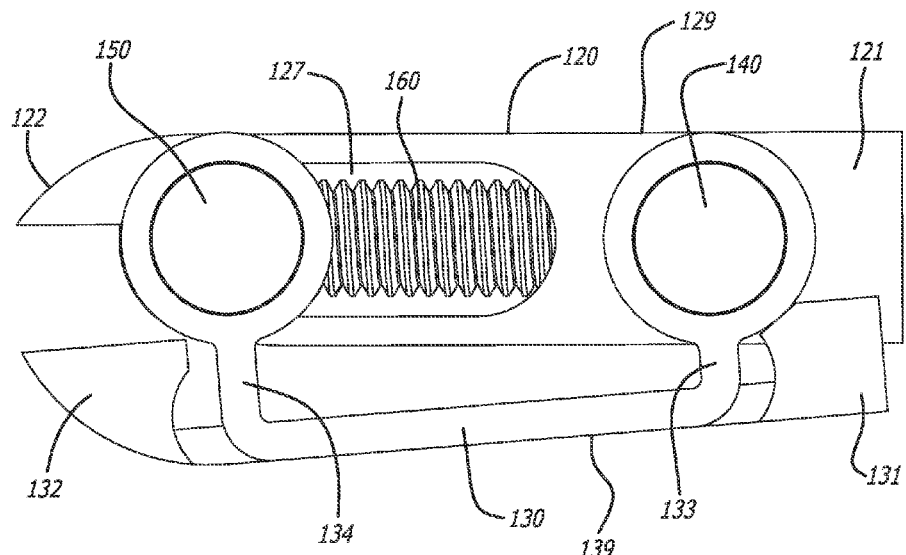
FIG. 16 is a side elevational view of the spinal implant of FIGS. 10-15 in the expanded configuration.
Figure 17:
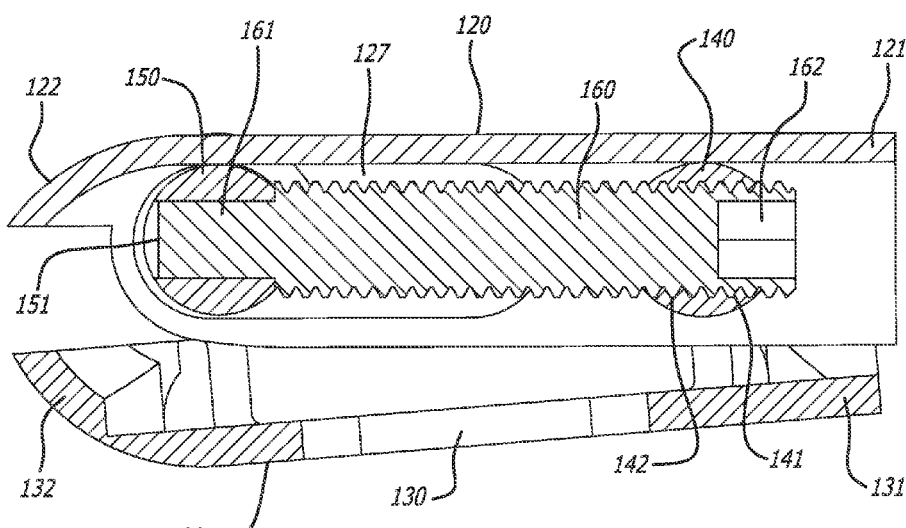
FIG. 17 is a cross-sectional view along Line 17-17 of FIG. 14 showing the spinal implant of FIGS. 10-16 in the expanded configuration.
Figure 26:
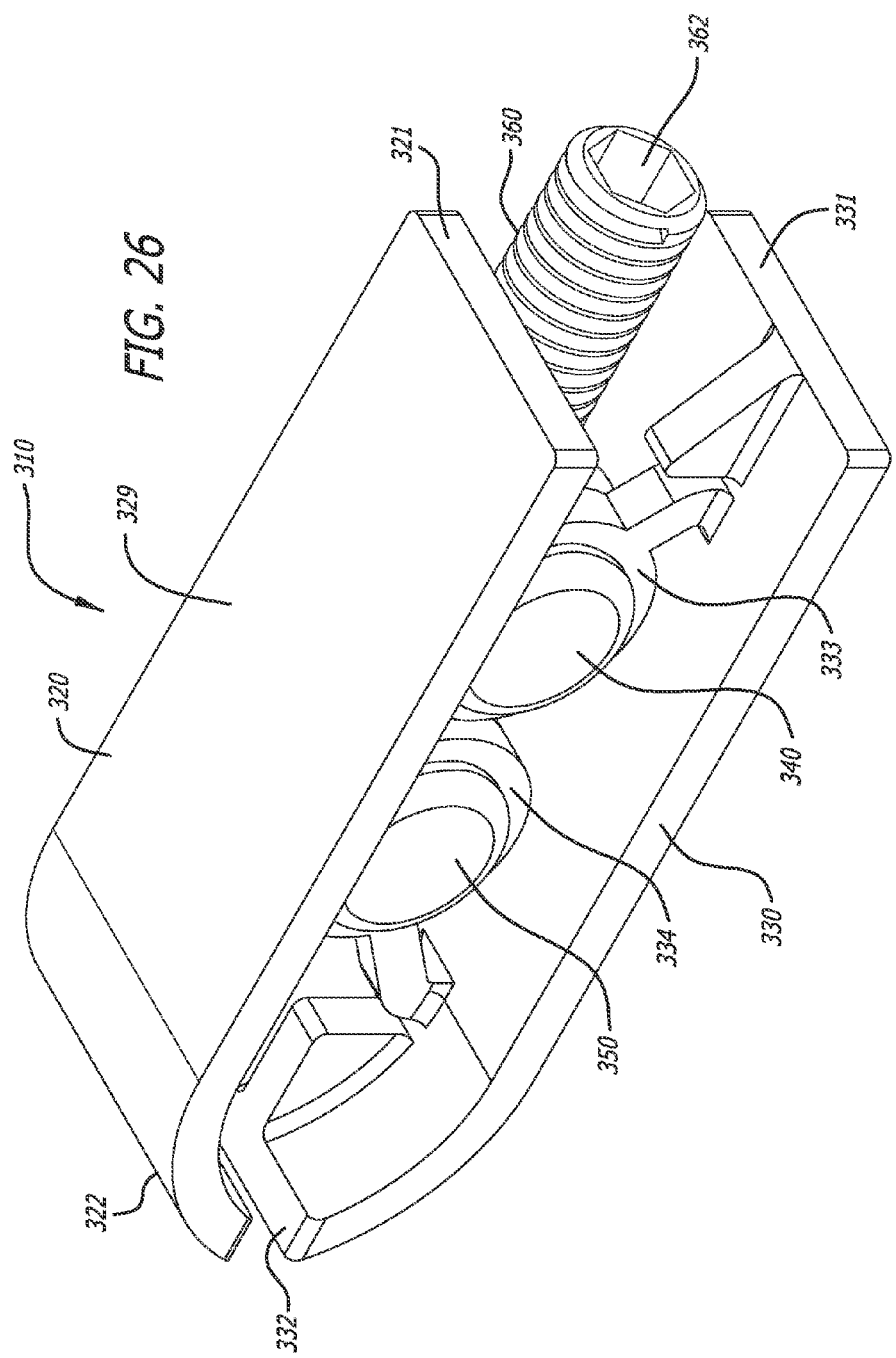
FIG. 26 is a rear perspective view of another embodiment of an expandable spinal implant in accordance with the invention in the unexpanded configuration.
Figure 27:
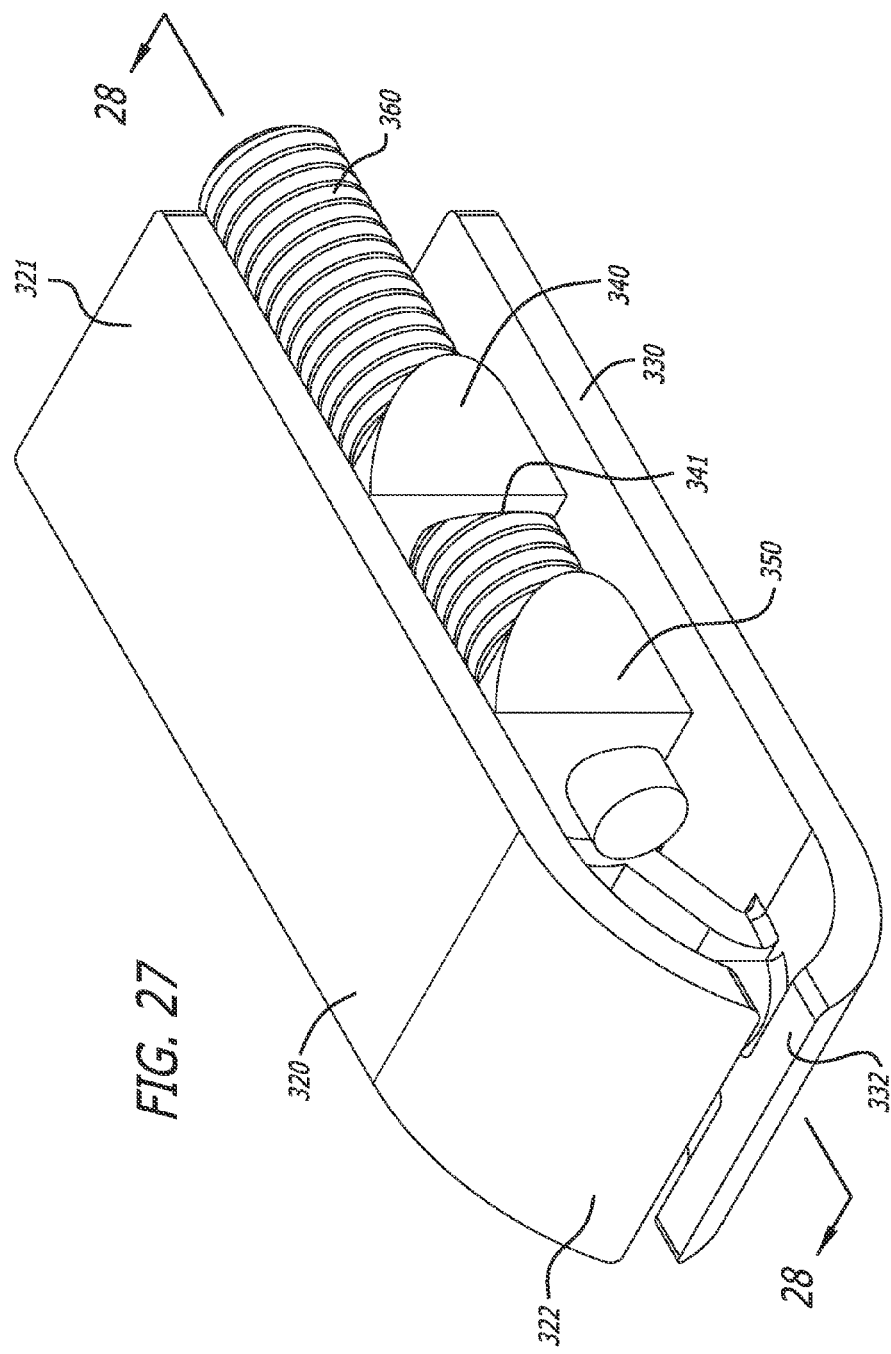
FIG. 27 is a front perspective view of the expandable spinal implant of FIG. 26 in the unexpanded configuration.
Figure 28:
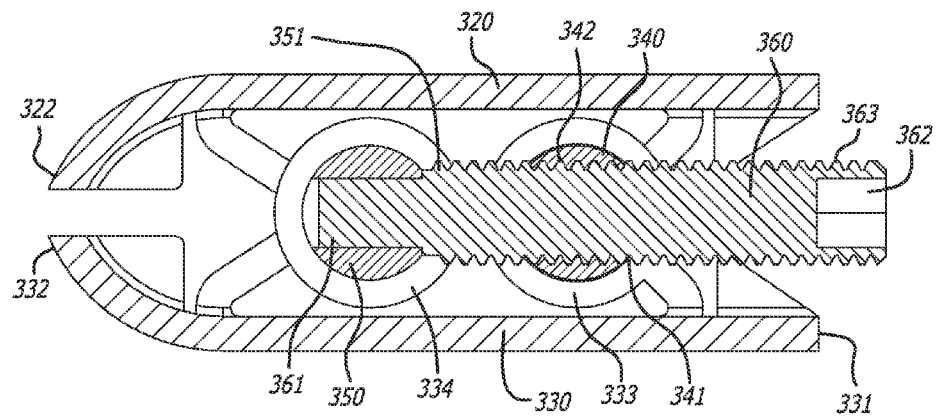
FIG. 28 is a side cross-sectional view along Line 28-28 of FIG. 27 showing the expandable spinal implant of FIG. 26 in the unexpanded configuration.
Figure 29:
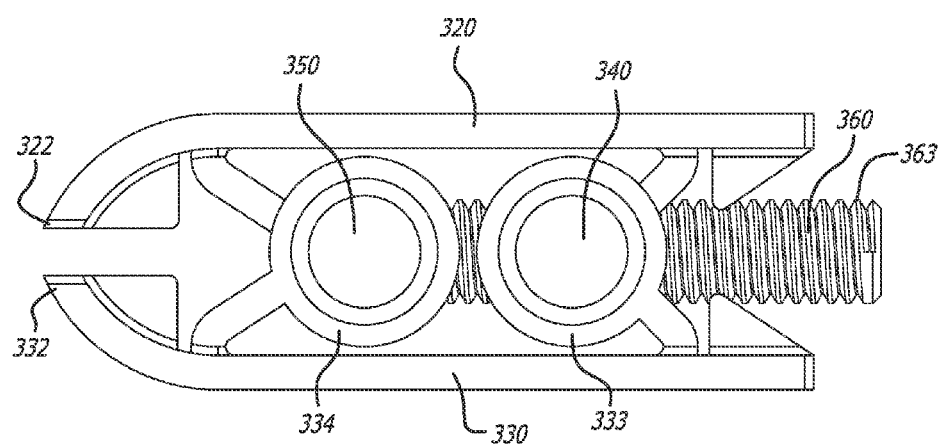
FIG. 29 is a side view of the expandable spinal implant of FIG. 26 in the unexpanded configuration.
Figure 30:
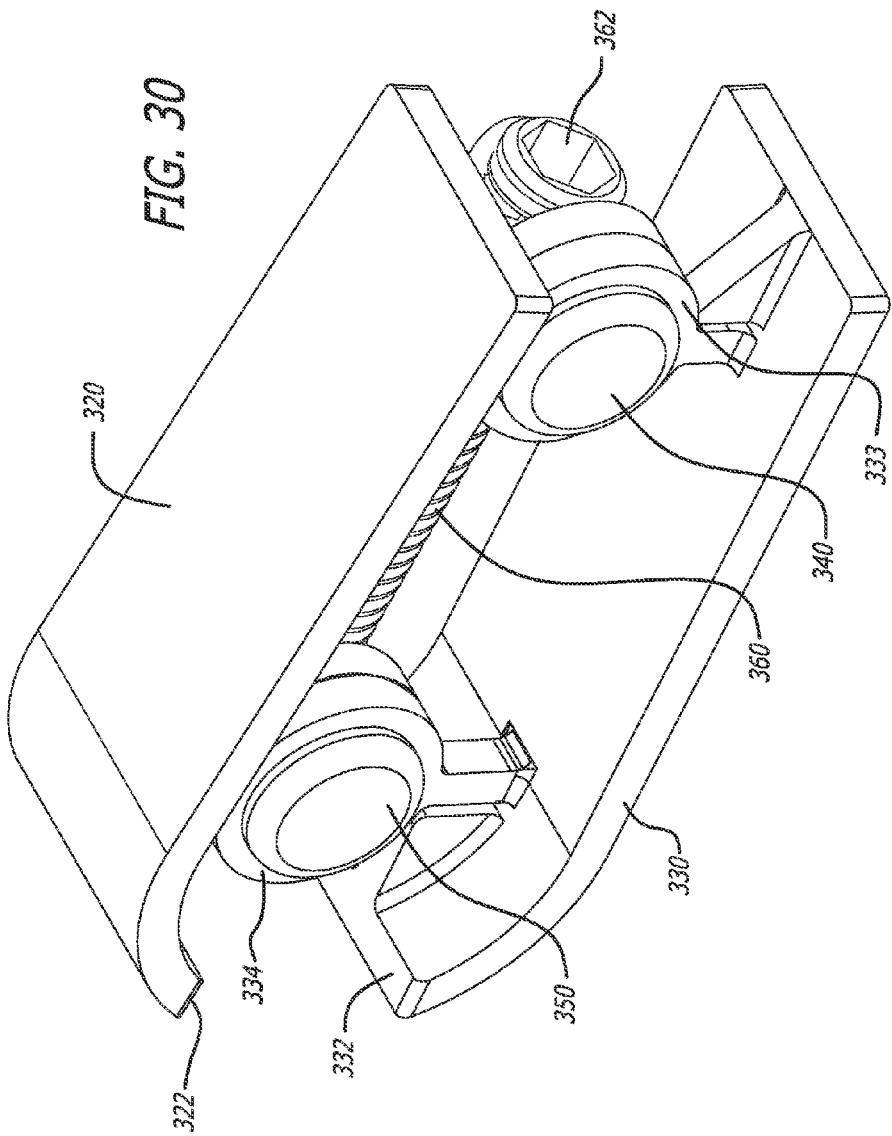
FIG. 30 is a rear perspective view of the expandable spinal implant of FIG. 26 in the expanded configuration.
Figure 31:
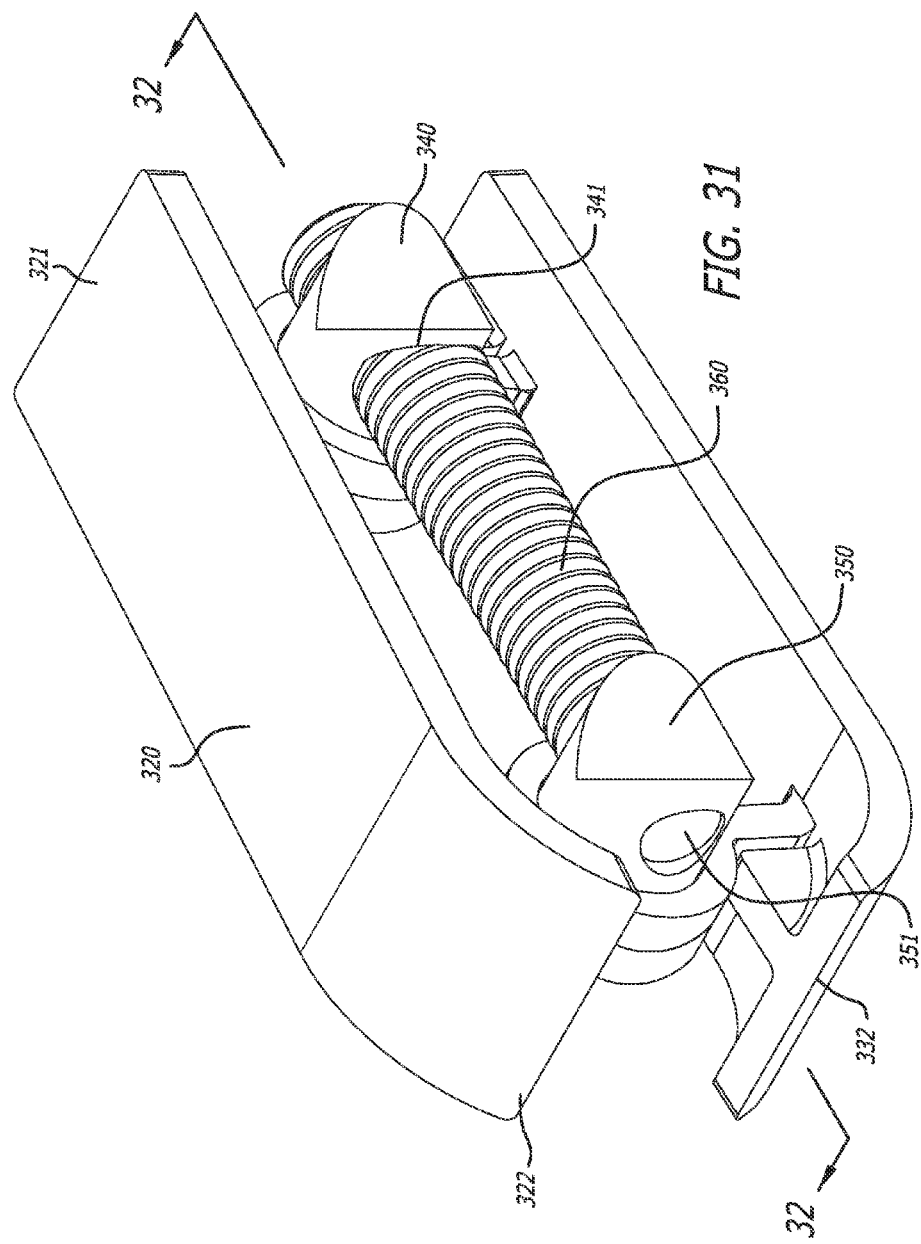
FIG. 31 is a front perspective view of the expandable spinal implant of FIG. 26 in the expanded configuration.
Figure 32:
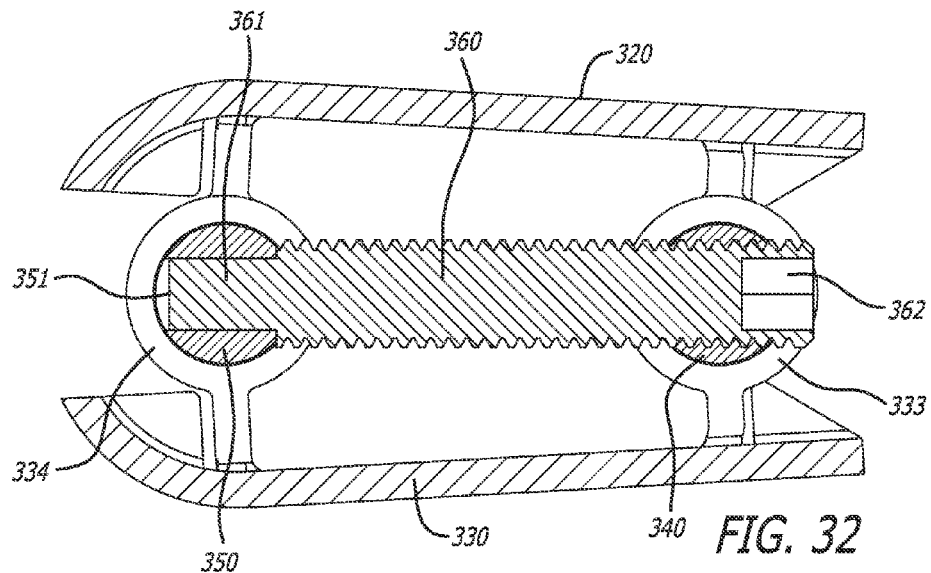
FIG. 32 is a side cross-sectional view along Line 32-32 of FIG. 31 showing the expandable spinal implant of FIG. 26 in the expanded configuration.
Figure 33:
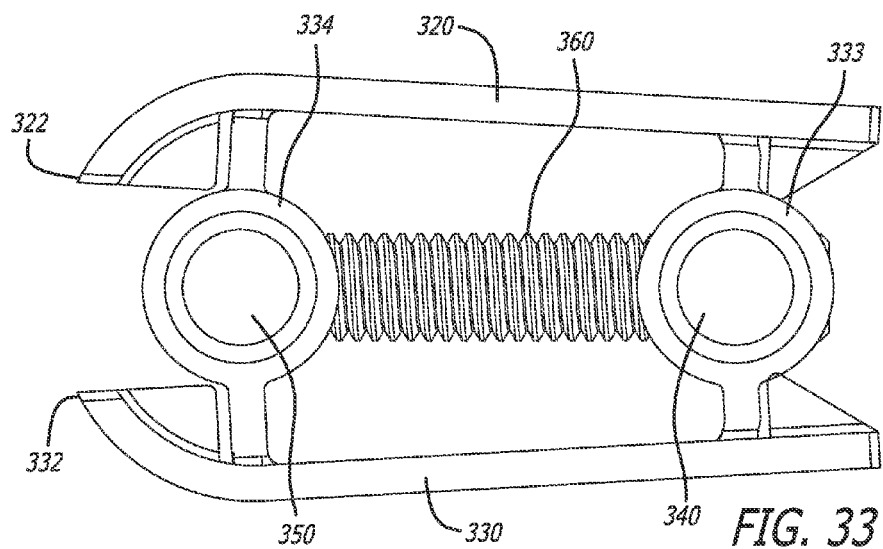
FIG. 33 is a side view of the expandable spinal implant of FIG. 26 in the expanded configuration.
Figure 34:
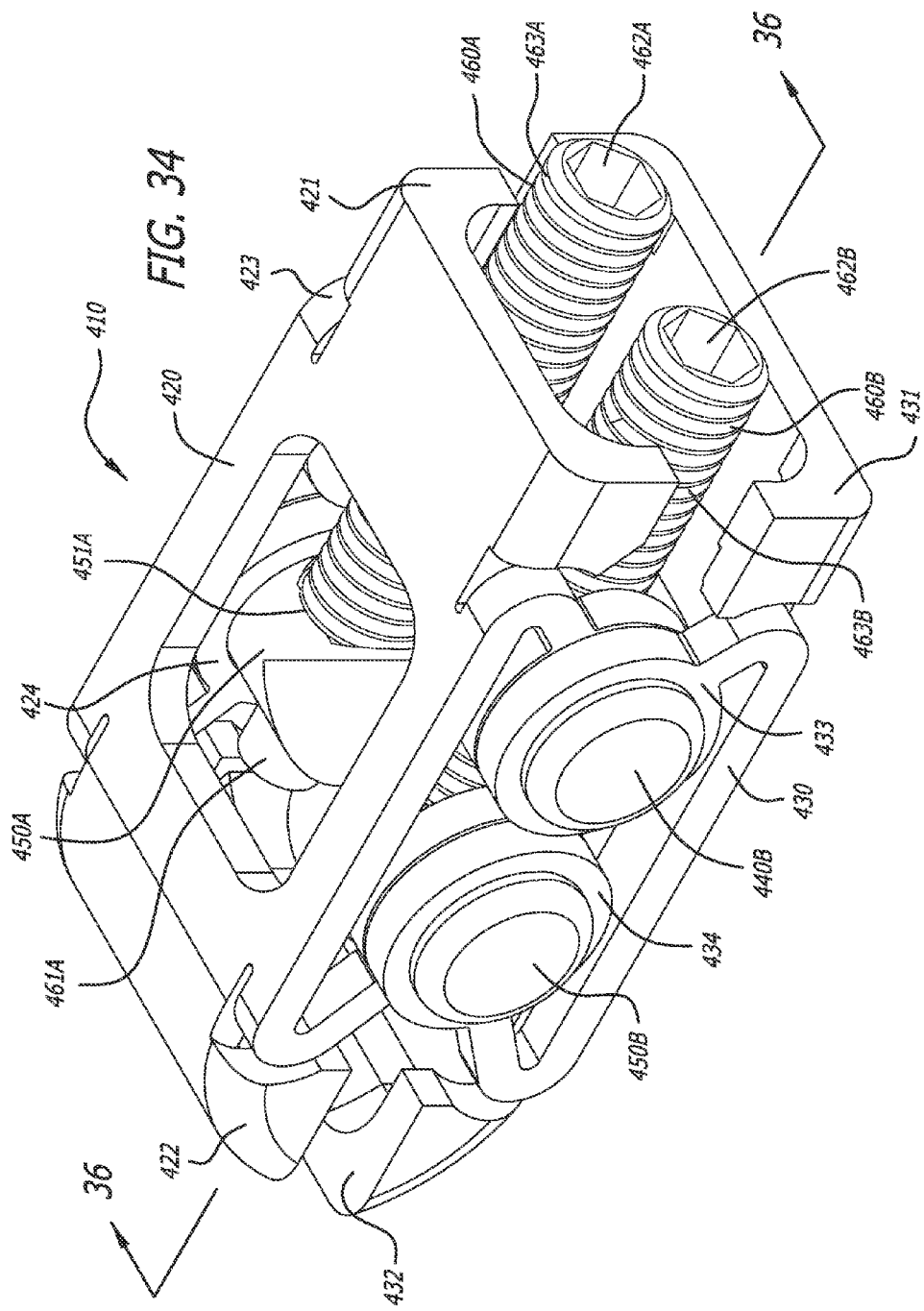
FIG. 34 is a rear perspective view of another embodiment of an expandable spinal implant in accordance with the invention in the unexpanded configuration.
Figure 35:
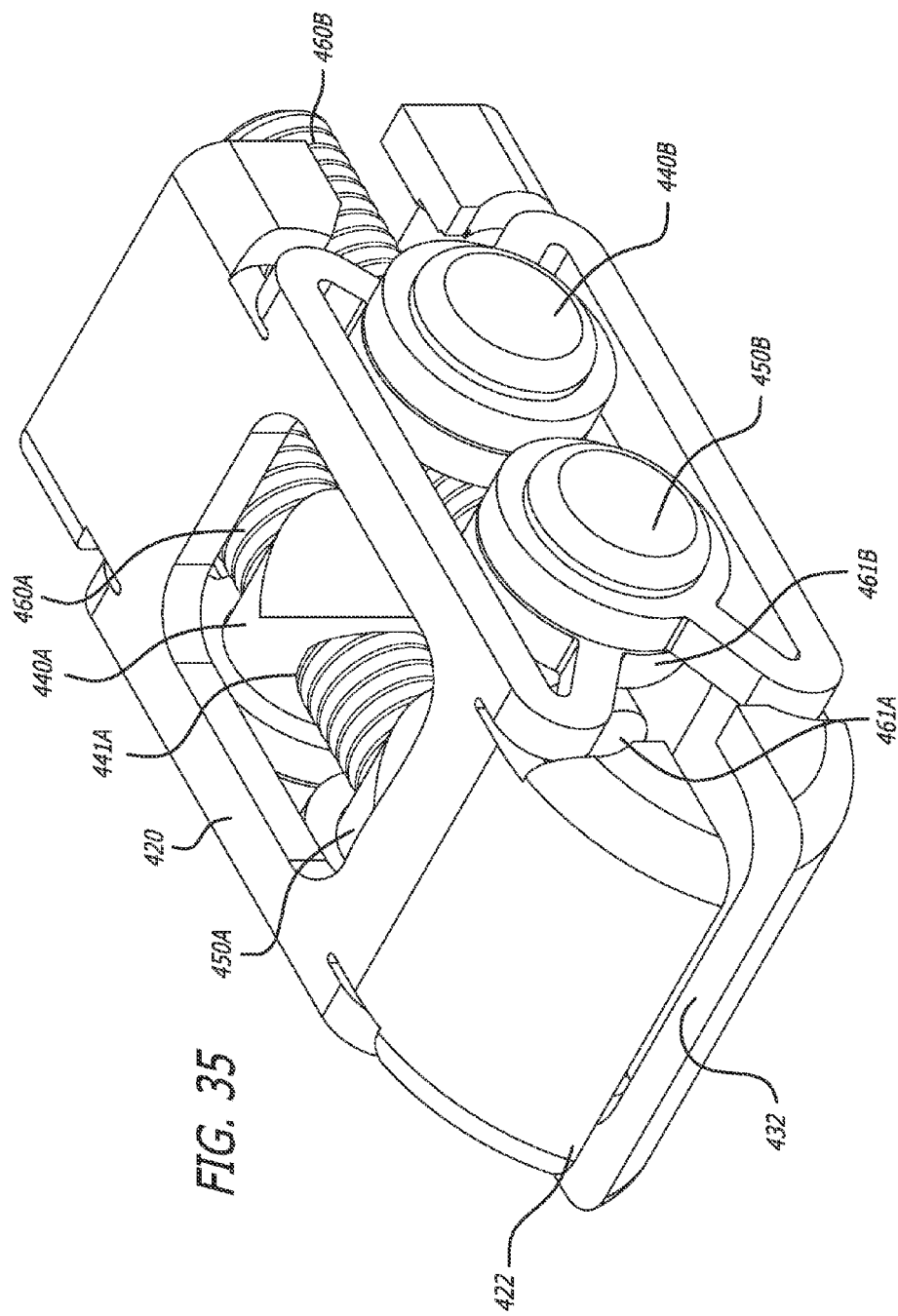
FIG. 35 is a front perspective view of the expandable spinal implant of FIG. 34 in the unexpanded configuration.
Figure 36:
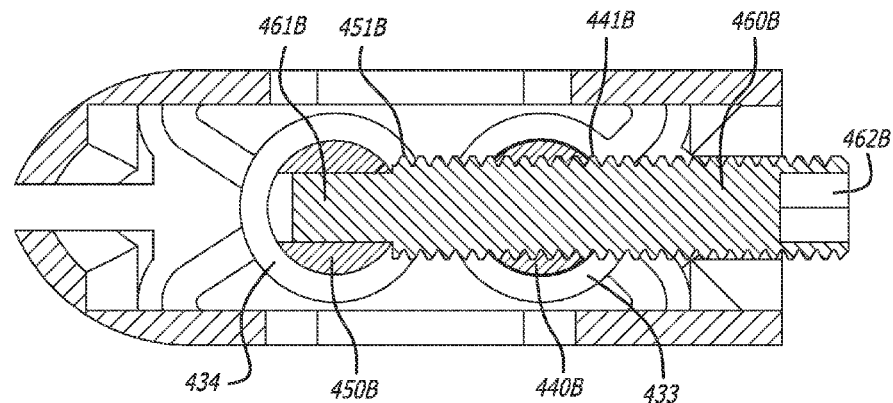
FIG. 36 is a side cross-sectional view along Line 36-36 of FIG. 34 showing the expandable spinal implant of FIG. 34 in the unexpanded configuration.
Figure 37:
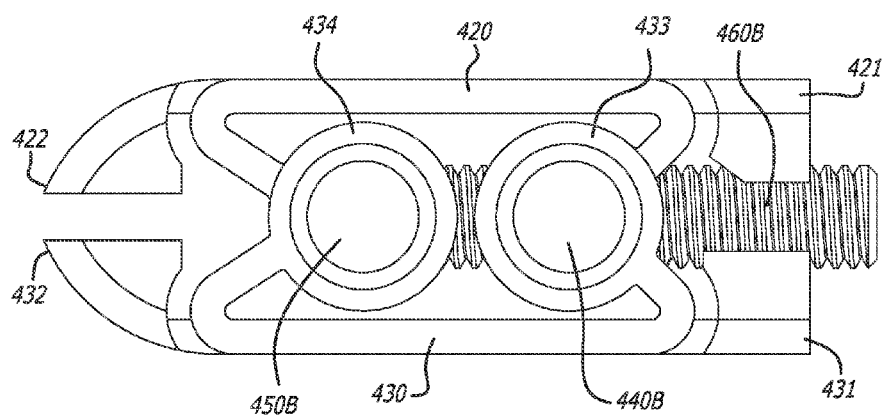
FIG. 37 is a side view of the expandable spinal implant of FIG. 34 in the unexpanded configuration.
Figure 38:
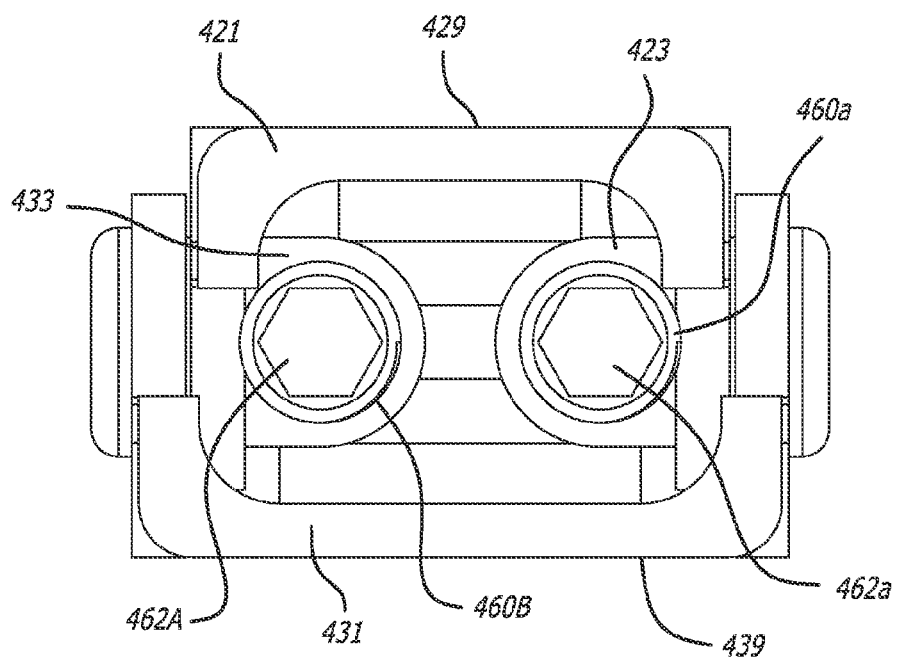
FIG. 38 is a rear view of the expandable spinal implant of FIG. 34 in the unexpanded configuration.

In accordance with the present invention, a first embodiment of an expandable spinal implant 10 is depicted in FIGS. 1-9. In accordance with the present invention, a second embodiment of an expandable spinal implant 110 is depicted in FIGS. 10-17, a third embodiment of an expandable spinal implant 210 is depicted in FIGS. 18-25, a fourth embodiment of an expandable implant 310 is depicted in FIGS. 26-33, and a fifth embodiment of an expandable implant 410 is depicted in FIGS. 34-44. As discussed below, each of the spinal implants 10, 110, 210, 310, and 410 may be plastically deformed to facilitate expansion thereof. Similar numerals are used to describe similar features of the expandable spinal implants 10, 110, 210, 310, and 410.

The spinal implants 10, 110, 210, 310, and 410 can be used as fusion implants, and are configured for placement in a disc space between two adjacent vertebrae. The spinal implants 10, 110, 210, 310, and 410 can be packed with fusion promoting materials to facilitate their use as spinal fusion cages. To that end, the spinal implants 10, 110, 210, 310, and 410 may include interior cavities (or chambers) for receiving the fusion promoting materials therein. Furthermore, as discussed below, the spinal implants 10, 110, 210, 310, and 410 can be moved from an unexpended configuration to an expanded configuration. In doing so, the implants 10, 110, 210, 310, and 410 can be used in producing an angular relationship between the two adjacent vertebrae corresponding to naturally occurring physiologic lordosis. Each of the expandable implants defines a mid-longitudinal axis.

As depicted in FIGS. 1-9, the spinal implant 10 includes a first plate 20, a second plate 30, a first transverse member 40, a second transverse member 50, and a screw 60. The first plate 20 includes a proximal end 21 and a distal end 22 opposite from one another, and a mid-longitudinal axis extending through the proximal end 21 and the distal end 22. The transverse member 40 is oriented transverse to the mid-longitudinal axis, whereas the screw 60 is oriented coaxial with the mid-longitudinal axis. The first plate 20 also includes a bone contacting surface 29 extending from the proximal end 21 to the distal end 22. The first plate 20 further includes an aperture 25 extending from the bone contacting surface 29 through the first plate 20 to allow for bone growth therethrough. The first plate 20 also includes a first link or pair of links 23 proximate the proximal end 21 of the first plate 20. The first plate 20 also includes a second link or pair of links 24 proximate the distal end 22 of the first plate 20. Although pairs of links 23 and 24 are preferred and depicted in the drawings, pairs of links are not required. Single links 23 or 24 are possible, and are within the scope of the present invention. The transverse members 40 and 50 preferably have cylindrical configurations, but other configurations, including but not limited to rectangular configurations, square configurations, or a single U-shaped configuration are possible, and are within the scope of the present invention.

Similar to the first plate 20, as depicted in FIGS. 1-9, the second plate 30 includes a proximal end 31 and a distal end 32 opposite from one another, and a mid-longitudinal axis extending through the proximal end 31 and the distal end 32. The second plate 30 also includes a bone contacting surface 39 extending from the proximal end 31 to the distal end 32. The second plate 30 further includes an aperture 35 extending from the bone contacting surface 39 through the second plate to allow for bone growth therethrough. The second plate 30 also includes a third link or pair of links 33 proximate the proximal end 31 of the second plate 30. The second plate 30 also includes a fourth link or pair of links 34 proximate the distal end 32 of the second plate 30.

The first transverse member 40 has the first link or pair of links 23 and the third link or pair of links 33 rotationally attached thereto. Although pairs of links 23 and 33 is preferred and depicted in the drawings, pairs of links are not required. Single links 23 or 33 are possible, and are within the scope of the invention. The transverse member 40 preferably has a cylindrical configuration, but other configurations, including but not limited to rectangular configurations, square configurations, or a single U-shaped configuration are possible, and are within the scope of the present invention. The first transverse member 40 includes an opening 41 extending therethrough, coaxial with the mid-longitudinal axis. The opening 41 includes threads 42 therein.

The second transverse member 50 has the second link or pair of links 24 and the fourth link or pair of links 34 rotationally attached thereto. Again, while a pair of links is preferred, single links 24 or 34 are possible, and are within the scope of the present invention. The transverse member 50 preferably has a cylindrical configuration, but a rectangular configuration, a square configuration, or a single U-shaped configuration are possible, and are within the scope of the present invention. The second transverse member 50 includes an opening 51 extending at least partially therein, coaxial with the mid-longitudinal axis. The opening 51 in some embodiments may include threads 52 therein.

The screw 60 includes threads 63 along a majority of the length thereof. Alternately, the threads 63 can be reverse-threaded. The threads 63 correspond to and mate with the threads 42 within the opening 41 of the first transverse member 40, and in some embodiments with the threads 52 within the second opening 51 of the second transverse member 50. The screw 60 also includes a threadless leading portion 61 sized to fit, and rotate freely, within the opening 51 of the second transverse member 50. The screw 60 also includes an opening 62 in the trailing end configured to receive an expansion tool (not shown) therein. The opening 62 may be shaped to accept a hex key, hexalobular key, or any other suitable driver configuration. The opening 62 may be provided on either end of the screw 60, and the key may drive the screw 60 either clockwise or counterclockwise.

As shown in FIGS. 1, 2, 4, and 5, the unexpanded configuration of the expandable spinal implant 10 includes the bone contacting surfaces 29, 39 of the first plate 20 and the second plate 30 aligned in a parallel orientation. The distal end 22 of first plate 20 and the distal end 32 of second plate 30 are both tapered, or convex, to facilitate insertion of the expandable spinal implant 10 into the disc space between two adjacent vertebrae. The central longitudinal axes of all four of the links or pairs of links 23, 24, 33, 34 form acute angles with the mid-longitudinal axes of their respective plates 20, 30.

The expandable spinal implant 10 is affixed to an insertion tool (not shown) which may closely match either the interior surfaces or exterior surfaces of the proximal ends 21 and 31 of the first and second plates 20 and 30. In addition, the proximal ends 21 and 31 of the first and second plates 20 and 30 may also include notches to cooperate with a detent mechanism located on the distal end of the inserter, thereby preventing relative motion between the expandable spinal implant 10 and the inserter until the expandable spinal implant 10 has been positioned correctly within the disc space and the detent is released via a control located on the proximal end of the inserter.

After the expandable spinal implant 10 is properly placed into the disc space, the expansion tool is inserted into the opening 62 of the screw 60 and the expansion tool is rotated to advance the screw 60 through the opening 41 of the first pin 40. As the screw 60 advances through the opening 41 of the first transverse member 40, threadless leading portion 61 rotates freely within the opening 51 of the second transverse member 50, and the shoulder where leading portion 61 abuts the threaded portion of the screw 60 applies a force against the second transverse member 50. The opposing forces generated by the screw threads 63 against the opening threads 42 and the shoulder against second transverse member 50 causes the first transverse member 40 to move toward the proximal ends 21, 31 of the plates 20, 30 and the second transverse member 50 to move toward the distal ends 22, 32 of the plates 20, 30. The movement of the transverse members causes the four pairs of rotationally attached links or pairs of links 23, 24, 33, 34 to rotate about the axes of rotation located proximate their respective bone contact surfaces. The rotation of the four links or pairs of links 23, 24, 33, 34 preferably causes the links to plastically deform, thereby enabling the links to maintain their new positions in the expanded configuration.

As shown in FIGS. 6-9, when the expandable spinal implant 10 is fully expanded, the central longitudinal axes of the links or pairs of links 23, 24, 33, 34 are approximately perpendicular to the bone contacting surfaces 29, 39 of the plates 20, 30. This is the preferred arrangement so as to provide optimal load transfer through the links or pairs of links 23, 24, 33, 34 prior to complete fusion of the joint. In order to prevent accidental overexpansion of the expandable spinal implant 10, the expansion tool (not shown) that is utilized to rotate the screw 60 may include a shroud that surrounds the trailing end of screw 60 while the tip of the expansion tool is inserted into the opening 62. The shroud should extend approximately as long as the tip of the expansion tool. As such, as the trailing end of the screw 60 advances into the opening 41 of the first transverse member 40, the shroud will encounter the first transverse member 40, and therefore, be prevented from further advancement. When the expandable spinal implant 10 has achieved full expansion, interference between the shroud and the first transverse member will prevent the tip of the expansion tool from being able reach into the opening 62, thereby preventing further rotation/advancement of the screw 60. In addition, the first transverse member 40 may include a groove surrounding the opening to cooperate with the shroud as it contacts the first transverse member to prevent the expansion tool from slipping laterally as the tip of the expansion tool is separated from the opening 41.

In the embodiment shown in the unexpanded configuration of FIGS. 1, 2, 4, and 5, the expandable spinal implant 10 is 24 mm long, 10 mm wide, and 8 mm tall. In the expanded configuration shown in FIGS. 6-9, the expandable spinal implant 10 is 12 mm tall at the distal ends 22, 32 and 9 mm tall at the proximal ends 21, 31, with a relative angle between the bone contacting surfaces 29, 39 of 10 degrees. This example would be appropriate for a PLIF procedure, wherein the distal ends 22, 32 are positioned proximate the anterior portions of the vertebral bodies. As such, the expanded configuration serves to restore the naturally occurring physiologic lordosis. However, the preceding sizes are merely an example, as the expandable spinal implant 10 could have a length between 10-30 mm, a width of 8 to 15 mm, an unexpanded height of 8 to 15 mm, and an expanded proximal height between 9 to 13 mm, with a relative angle between the bone contacting surfaces 29, 39 of 0-25 degrees. The total height of the expansion and the relative angle between the bone contacting surfaces 29, 39 is determined by the lengths of the four links or pairs of links. For example, if the links are all uniform in length the bone contacting surfaces 29, 39 of the plates 20, 30 will maintain a parallel relationship after expansion. In addition, for a DLIF procedure, it may be desirable for the bone contacting surfaces 29, 39 to be angled relative to each other along the width rather than the length. This configuration could be accomplished by having longer links or pairs of links on one side.

It may be desirable to further modify the expandable implant 10 such that the bone contacting surfaces 29, 39 are convex or biconvex, in order to mimic the shapes of the endplates of the adjacent vertebrae. In addition, it may be desirable to add bone engaging projections to the bone contacting surfaces 29, 39, in order to prevent unwanted migration of the expandable spinal implant 10 prior to achieving the desired fusion.

The expandable spinal implant 10 is preferably made of a machined or milled metal, including but not limited to titanium, stainless steel and/or nickel-titanium shape memory materials (trade name NITINOL) suitable for implantation within the body. Alternatively the expandable spinal implant 10 can be made from a biocornpaiible polymer (such as PEEK, for example). In some such embodiments, the biocompatible polymer may be provided with a titanium coating at selected areas (such as areas in contact with vertebral endplates), and/or radiopaque markers to establish the position and/or orientation of the implant under radiographic observation. However, the expandable spinal implant 10 may be constructed of any material suitable for implantation or a combination of those materials.

After insertion and expansion of the expandable spinal implant 10, it may be desirable to fill the space between the first and second plates 20, 30 with a fusion promoting substance to facilitate its use as a spinal fusion cage.

As depicted in FIGS. 10-17, the spinal implant 110 includes a first plate 120, a second plate 130, a first transverse member 140, a second transverse member 150, and a screw 160. The first plate 120 includes a proximal end 121 and a distal end 122 opposite from one another, and a mid-longitudinal axis extending through the proximal end 121 and the distal end 122. The first plate 120 also includes a bone contacting surface 129 extending from the proximal end 121 to the distal end 122. The first plate 120 also includes sidewalls extending down from the bone contacting surface 129. The sidewalls include a first pair of openings (not shown) proximate the proximal end 121 of the first plate 120. The first plate 120 also includes a second pair of openings 127 proximate the distal end 122 of the first plate 120.

Similar to the first plate 120, the second plate 130 includes a proximal end 131 and a distal end 132 opposite from one another, and a mid-longitudinal axis extending through the proximal end 131 and the distal end 132. The second plate 130 also includes a bone contacting surface 139 extending from the proximal end 131 to the distal end 132. The second plate 130 further includes an aperture 135 extending from the bone contacting surface 139 through the second plate to allow for bone growth therethrough. The second plate 130 also includes a first link or pair of links 133 proximate the proximal end 131 of the second plate 130. The second plate 130 also includes a second link or pair of links 134 proximate the distal end 132 of the second plate 130.

The first transverse member 140 has the first link or pair of links 133 rotationally attached thereto. The first transverse member 140 extends through the first pair of openings in the first plate 120. The first transverse member 140 includes an opening 141 extending therethrough, the opening 141 including threads 142 therein.

The second transverse member 150 has the second link or pair of links 134 rotationally attached thereto. The second transverse member 150 extends through the second pair of openings 127 in the first plate 120. The second transverse member 150 includes an opening 151 extending at least partially therein.

The screw 160 includes threads 163 along a majority of the length thereof. The threads 163 correspond to and mate with the threads 142 within the opening 141 of the first transverse member 140. The screw 160 also includes a threadless leading portion 161 sized to fit, and rotate freely, within the opening 151 of the second transverse member 150. The screw 160 also includes an opening 162 in the trailing end configured to receive an expansion tool (not shown) therein. The opening may be shaped to accept a hex key, hexalobular key, or any other suitable driver configuration.

As shown in FIGS. 10-13, the unexpanded configuration of the expandable spinal implant 110 includes the bone contacting surfaces 129, 139 of the first plate 120 and the second plate 130 aligned in a parallel orientation. The distal end 122 of first plate 120 and the distal end 132 of second plate 130 are both tapered, or convex, to facilitate insertion of the expandable spinal implant 110 into the disc space between the two adjacent vertebrae. The central longitudinal axes of both of the links or pairs of links 133, 134 form acute angles with the mid-longitudinal axis of the second plate 130.

The expandable spinal implant 110 is affixed to an insertion tool (not shown) which may closely match either the interior surfaces or exterior surfaces of the proximal ends 121 and 131 of the first and second plates 120 and 130. In addition, the proximal ends 121 and 131 of the first and second plates 120 and 130 may also include notches to cooperate with a detent mechanism located on the distal end of the inserter, thereby preventing relative motion between the expandable spinal implant 110 and the inserter until the expandable spinal implant 110 has been positioned correctly within the disc space and the detent is released via a control located on the proximal end of the inserter.

After the expandable spinal implant 110 is properly placed into the disc space, the expansion tool is inserted into the opening 162 of the screw 160 and the expansion tool is rotated to advance the screw 160 through the opening 141 of the first transverse member 140. As the screw 160 advances through the opening 141 of the first transverse member 140, threadless leading portion 161 rotates freely within the opening 151 of the second transverse member 150, and the shoulder where leading portion 161 abuts the threaded portion of the screw 160 applies a force against the second transverse member 150. The opposing forces generated by the screw threads 163 against the opening threads 142 and the shoulder against second transverse member 150 causes the first transverse member 140 to move toward the proximal end 131 of the second plate 130 and the second transverse member 150 to move toward the distal ends 122, 132 of the first and second plates 120, 130. Because the first transverse member 140 is in a fixed relationship with the first plate 120 and the second transverse member 150 is free to translate within the second pair of openings 127, the separation of the first and second transverse members 140, 150 causes the first plate 120 to translate toward the proximal end 131 the second plate 130. The movement of the transverse members 140, 150 causes the two rotationally attached links or pairs of rotationally attached links 133, 134 to rotate about the axes of rotation located proximate the bone contact surface of the second plate. The rotation of the two links or pairs of links 133, 134 preferably causes the links or pairs of links to plastically deform, thereby enabling the links or pairs of links to maintain their new positions in the expanded configuration.

As shown in FIGS. 14-17, when the expandable spinal implant 110 is fully expanded, the links or pairs of links 133, 134 are approximately perpendicular to the bone contacting surface 139 of the second plate 130. This is the preferred arrangement so as to provide optimal load transfer through the links or pairs of links 133, 134 prior to complete fusion of the joint. In order to prevent accidental overexpansion of the expandable spinal implant 110, the expansion tool (not shown) that is utilized to rotate the screw 160 may include a shroud that surrounds the trang end of screw 160 while the tip of the expansion tool is inserted into the opening 162. The shroud should extend approximately as long as the tip of the expansion tool. As such, as the trailing end of the screw 160 advances into the opening 141 of the first transverse member 140, the shroud will encounter the first transverse member 140, and therefore, be prevented from further advancement. When the expandable spinal implant 110 has achieved full expansion, interference between the shroud and the first transverse member will prevent the tip of the expansion tool from being able reach into the opening 162, thereby preventing further rotation/advancement of the screw 160. In addition, the first transverse member 140 may include a groove surrounding the opening to cooperate with the shroud as it contacts the first transverse member to prevent the expansion tool from slipping laterally as the tip of the expansion tool is separated from the opening 141.

In addition to being useful for restoring lordosis or kyphosis, the relative translation of the first and second plates 120, 130 may be useful for spondylosthesis reduction.

It may be desirable to further modify the expandable implant 110 such that the bone contacting surfaces 129, 139 are convex or biconvex, in order to mimic the shapes of the endplates of the adjacent vertebrae. In addition, it may be desirable to add bone engaging projections to the bone contacting surfaces 129, 139, in order to prevent unwanted migration of the expandable spinal implant 110 prior to achieving the desired fusion.

The expandable spinal implant 110 is preferably made of a machined or milled metal, including but not limited to titanium, stainless steel and/or nickel-titanium shape memory materials (trade name NITINOL) suitable for implantation within the body. Alternatively the expandable spinal implant 110 can be made from a biocompatible polymer (such as PEEK, for example). In some such embodiments, the biocompatible polymer may be provided with a titanium coating at selected areas (such as areas in contact with vertebral endplates), and/or radiopaque markers to establish the position and/or orientation of the implant under radiographic observation. However, the expandable spinal implant 110 may be constructed of any material suitable for implantation or a combination of those materials.

After insertion and expansion of the expandable spinal implant 110, it may be desirable to fill the space between the first and second plates 120, 130 with a fusion promoting substance to facilitate its use as a spinal fusion cage.

As depicted in FIGS. 18-25, the spinal implant 210 includes a first plate 220, a second plate 230, a first transverse member 240, a second transverse member 250, and a screw 260. The first plate 220 includes a proximal end 221 and a distal end 222 opposite from one another, and a mid-longitudinal axis extending through the proximal end 221 and the distal end 222. The first plate 220 also includes a bone contacting surface 229 extending from the proximal end 221 to the distal end 222. The first plate 220 further includes a first link 223 or first pair of links 223 proximate the proximal end 221 of the first plate 220. The first plate 220 also includes a second link 224 or second pair of links 224 proximate the distal end 222 of the first plate 220.

Similar to the first plate 220, the second plate 230 includes a proximal end 231 and a distal end 232 opposite from one another, and a mid-longitudinal axis extending through the proximal end 231 and the distal end 232. The second plate 230 also includes a bone contacting surface 239 extending from the proximal end 231 to the distal end 232. The second plate 230 further includes a third link 233 or third pair of links 233 proximate the proximal end 231 of the second plate 230. The second plate 230 also includes a fourth link 234 or fourth pair of links 234 proximate the distal end 232 of the second plate 230.

The first transverse member 240 has the first link 223 or first pair of links 223 and the third link 233 or third pair of links 233 rotationally attached thereto. The first transverse member 240 includes an opening 241 extending therethrough, the opening 241 including threads 242 therein.

The second transverse member 250 has the second link 224 or second pair of links 224 and the fourth link 234 or fourth pair of links 234 rotationally attached thereto. The second transverse member 250 includes an opening 251 extending at least partially therein.

The screw 260 includes threads 263 along a majority of the length thereof. The threads 263 correspond to and mate with the threads 242 within the opening 241 of the first transverse member 240. The screw 260 also includes a threadless leading portion 261 sized to fit, and rotate freely, within the opening 251 of the second transverse member 250. The screw 260 also includes an opening 262 in the trailing end configured to receive an expansion tool (not shown) therein. The opening may be shaped to accept a hex key, hexalobular key, or any other suitable driver configuration.

As shown in FIGS. 18-24, the links or pairs of links 223, 224, 233, 234, the transverse members 240, 250, and the screw 260 are angled relative the bone contacting surfaces 229, 239. This is to enable access to the screw 260 when the expandable spinal implant 210 is inserted into the disc space during an ALIF or OLE procedure.

As shown in FIGS. 18-21, the unexpanded configuration of the expandable spinal implant 210 includes the bone contacting surfaces 229, 239 of the first plate 220 and the second plate 230 positioned in an angled orientation. The distal end 222 of first plate 220 and the distal end 232 of second plate 230 are both tapered, or convex, to facilitate insertion of the expandable spinal implant 210 into the disc space between two vertebrae. The central longitudinal axes of all four of the links or pairs of links 223, 224, 233, 234 form acute angles with the mid-longitudinal axes of their respective plates 220, 230.

The expandable spinal implant 210 is affixed to an insertion tool (not shown) which may closely match either the interior surfaces or exterior surfaces of the proximal ends 221 and 231 of the first and second plates 220 and 230. In addition, the proximal ends 221 and 231 of the first and second plates 220 and 230 may also include notches to cooperate with a detent mechanism located on the distal end of the inserter, thereby preventing relative motion between the expandable spinal implant 210 and the inserter until the expandable spinal implant 210 has been positioned correctly within the disc space and the detent is released via a control located on the proximal end of the inserter.

After the expandable spinal implant 210 is properly placed into the disc space, the expansion tool is inserted into the opening 262 of the screw 260 and the expansion tool is rotated to advance the screw 260 through the opening 241 of the first transverse member 240. As the screw 260 advances through the opening 241 of the first transverse member, threadless leading portion 261 rotates freely within the opening 251 of the second transverse member 250, and the shoulder where leading portion 261 abuts the threaded portion of the screw 260 applies a force against the second transverse member 250. The opposing forces generated by the screw threads 263 against the opening threads 242 and the shoulder against second transverse member 250 causes the first transverse member 240 to move toward the proximal ends 221, 231 of the plates 220, 230 and the second transverse member 250 to move toward the distal ends 222, 232 of the plates 220, 230. The movement of the transverse members causes the four rotationally attached links or four pairs of rotationally attached links 223, 224, 233, 234 to rotate about the axes of rotation located proximate their respective bone contact surfaces. The rotation of the four links or pairs of links 223, 224, 233, 234 preferably causes the links or pairs of links to plastically deform, thereby enabling the links or pairs of links to maintain their new positions in the expanded configuration.

As shown in FIGS. 22-25, when the expandable spinal implant 210 is fully expanded, the links or pairs of links 223, 224, 233, 234 are approximately parallel to each other. This is the preferred arrangement so as to provide optimal load transfer through the links or pairs of links 223, 224, 233, 234 prior to complete fusion of the joint. In order to prevent accidental overexpansion of the expandable spinal implant 210, the expansion tool (not shown) that is utilized to rotate the screw 260 may include a shroud that surrounds the trailing end of screw 260 while the tip of the expansion tool is inserted into the opening 262. The shroud should extend approximately as long as the tip of the expansion tool. As such, as the trading end of the screw 260 advances into the opening 241 of the first transverse member 240, the shroud will encounter the first transverse member 240, and therefore, be prevented from further advancement. When the expandable spinal implant 210 has achieved full expansion, interference between the shroud and the first transverse member will prevent the tip of the expansion expansion tool from being able reach into the opening 262, thereby preventing further rotation/advancement of the screw 260. In addition, the first transverse member 240 may include a groove surrounding the opening to cooperate with the shroud as it contacts the first transverse member to prevent the expansion tool from slipping laterally as the tip of the expansion tool is separated from the opening 241.

It may be desirable to further modify the expandable implant 210 such that the bone contacting surfaces 229, 239 are convex or biconvex, in order to mimic the shapes of the endplates of the adjacent vertebrae. In addition, it may be desirable to add bone engaging projections to the bone contacting surfaces 229, 239, in order to prevent unwanted migration of the expandable spinal implant 210 prior to achieving the desired fusion.

The expandable spinal implant 210 is preferably made of a machined or milled metal, including but not limited to titanium, stainless steel and/or nickel-titanium shape memory materials (trade name NITINOL) suitable for implantation within the body. Alternatively the expandable spinal implant 210 can be made from a biocompatible polymer (such as PEEK, for example). In some such embodiments, the biocompatible polymer may be provided with a titanium coating at selected areas (such as areas in contact with vertebral endplates), and/or radiopaque markers to establish the position and/or orientation of the implant under radiographic observation. However, the expandable spinal implant 210 may be constructed of any material suitable for implantation or a combination of those materials.

After insertion and expansion of the expandable spinal implant 210, it may be desirable to fill the space between the first and second plates 220, 230 with a fusion promoting substance to facilitate its use as a spinal fusion cage.

As depicted in FIGS. 26-33, a spinal implant 310 includes a first plate 320, a second plate 330, a first transverse members 340, a second transverse member 350, and the screw 360. The first plate 320 includes a proximal end 321 and a distal end 322 opposite from one another, and a mid-longitudinal axis extending through the proximal end 321 and the distal end 322. The first plate 320 also includes a bone contacting surface 329 extending from the proximal end 321 to the distal end 322. The first plate 320 further includes a first link 323 or first pair of links 323 proximate the proximal end 321 of the first plate 320. The first plate 320 also includes a second link 324 or second pair of links 324 proximate the distal end 322 of the first plate 320.

Similar to the first plate 320, the second plate 330 includes a proximal end 331 and a distal end 332 opposite from one another, and a mid-longitudinal axis extending through the proximal end 331 and the distal end 332. The second plate 330 also includes a bone contacting surface 339 extending from the proximal end 331 to the distal end 332. The second plate 330 further includes a third link 333 or third pair of links 333 proximate the proximal end 331 of the second plate 330. The second plate 330 also includes a fourth link 332 or fourth pair of links 334 proximate the distal end 332 of the second plate 330.

The first transverse member 340 has the first link 323 or first pair of links 323 and the third link 333 or third pair of links 333 rotationally attached thereto. The first transverse member 340 includes an opening 341 extending therethrough, the opening 341 including threads 342 therein.

The second transverse member 350 has the second link 324 or second pair of links 324 and the fourth link 334 or fourth pair of links 334 rotationally attached thereto. The second transverse member 350 includes an opening 351 extending at least partially therein.

The first link 323 or first pair of links 323, the second link 324 or second pair of links 324, the third link 333 or third pair of links 333, the fourth link 334 or fourth pair of links 334 are each centrally located on the first plate 320 and the second plate 330.

The screw 360 includes threads 363 along a majority of the length thereof. The threads 363 correspond to mate with the threads 342 within the opening 341 of the first transverse member 340. The screw 360 also includes a threadless leading portion 361 sized to fit, and rotate freely, within the opening 351 of the second transverse member 350. The screw 360 also includes an opening 362 in the trading end figured to receive an expansion tool (not shown) therein. The opening may be shaped to accept a hex key, hexalobular key, or any other suitable driver configuration.

As shown in FIGS. 26-29, the unexpanded configuration of the expandable spinal implant 310 includes the bone contacting surfaces 329, 339 of the first plate 320 and the second plate 330 aligned in a parallel orientation. The distal end 322 of first plate 320 and the distal end 332 of second plate 330 are both tapered, or convex, to facilitate insertion of the expandable spinal implant 310 into the disc space between the two adjacent vertebrae. The central longitudinal axes of both of the links or pairs of links 333, 334 form acute angles with the mid-longitudinal axis of the second plate 330.

The expandable spinal implant 310 is affixed to an insertion tool (not shown) which may closely match either the interior surfaces or exterior surfaces of the proximal ends 321 and 331 of the first and second plates 320 and 330. In addition, the proximal ends 321 and 331 of the first and second plates 320 and 330 may also include notches to cooperate with a detent mechanism located on the distal end of the inserter, thereby preventing relative motion between the expandable spinal implant 310 and the inserter until the expandable spinal implant 310 has been positioned correctly within the disc space and the detent is released via a control located on the proximal end of the inserter.

After the expandable spinal implant 310 is properly placed into the disc space, the expansion tool is inserted into the opening 362 of the screw 360 and the expansion tool is rotated to advance the screw 360 through the opening 341 of the first transverse member 340. As the screw 360 advances through the opening 341 of the first transverse member 340, threadless leading portion 361 rotates freely within the opening 351 of the second transverse member 350, and the shoulder where leading portion 361 abuts the threaded portion of the screw 360 applies a force against the second transverse member 350. The opposing forces generated by the screw threads 363 against the opening threads 342 and the shoulder against second transverse member 350 causes the first transverse member 340 to move toward the proximal end 331 of the second plate 330 and the second transverse member 350 to move toward the distal ends 322, 332 of the first and second plates 320, 330. The first transverse member 340 is in a fixed translational relationship with the first plate 320, i.e. first transverse member 340 may rotate within the first pair of openings but the first transverse member cannot translate relative to the first plate. However, because the second transverse member 350 is free to translate within the second pair of openings 351, the separation of the first and second transverse members 340, 350 causes the first plate 320 to translate toward the proximal end 331 of the second plate 330. The movement of the transverse members 340, 350 causes the two centrally-located rotationally attached links or pairs of rotationally attached links 333, 334 to rotate about the axes of rotation located proximate the bone contacting surface of the second plate 330. The rotation of the two links or pairs of links 333, 334 preferably causes the centrally-located links or pairs of links to plastically deform, thereby enabling the links or pairs of links to maintain their new positions in the expanded configuration.

As shown in FIGS. 30-33, when the expandable spinal implant 310 is fully expanded, the centrally-located links or pairs of links 333, 334 are approximately perpendicular to the bone contacting surface 339 of the second plate 330. This is the preferred arrangement so as to provide optimal load transfer through the centrally-located links or pairs of links 333, 334 prior to complete fusion of the joint. In order to prevent accidental overexpansion of the expandable spinal implant 310, the expansion tool (not shown) that is utilized to rotate the screw 360 may include a shroud that surrounds the trailing end of screw 360 while the tip of the expansion tool is inserted into the opening 362. The shroud should extend approximately as long as the tip of the expansion tool. As such, as the trailing end of the screw 360 advances into the opening 341 of the first transverse member 340, the shroud will encounter the first transverse member 340, and therefore, be prevented from further advancement. When the expandable spinal implant 310 has achieved full expansion, interference between the shroud and the first transverse member will prevent the tip of the expansion tool from being able to reach into the opening 362, thereby preventing further rotation/advancement of the screw 360. In addition, the first transverse member 340 may include a groove surrounding the opening to cooperate with the shroud as it contacts the first transverse member to prevent the expansion tool from slipping laterally as the tip of the expansion tool is separated from the opening 362.

In addition to being useful for restoring lordosis or kyphosis, the relative translation of the first and second plates 320, 330 may be useful for spondylosthesis reduction.

It may be desirable to further modify the expandable implant 310 such that the bone contacting surfaces 329, 339 are convex or biconvex, in order to mimic the shapes of the endplates of the adjacent vertebrae. In addition, it may be desirable to add bone engaging projections to the bone contacting surfaces 329, 339, in order to prevent unwanted migration of the expandable spinal implant 310 prior to achieving the desired fusion.

The expandable spinal implant 310 is preferably made of a machined or milled metal, including but not limited to titanium, stainless steel and/or nickel-titanium shape memory materials (trade name NITINOL) suitable for implantation within the body. Alternatively the expandable spinal implant 310 can be made from a biocompatible polymer (such as PEEK, for example). In some such embodiments, the biocompatible polymer may be provided with a titanium coating at selected areas (such as areas in contact with vertebral endplates), and/or radiopaque markers to establish the position and/or orientation of the implant under radiographic observation. However, the expandable spinal implant 310 may be constructed of any material suitable for implantation or a combination of those materials.

After insertion and expansion of the expandable spinal implant 310, it may be desirable to fill the space between the first and second plates 320, 330 with a fusion promoting substance to facilitate its use as a spinal fusion cage.

As depicted in FIGS. 34-44, a spinal implant 410 includes a first plate 420, a second plate 430, first transverse members 440A and 440B, second transverse members 450A and 450B, and two side-by side screws screw 460A and 460B. The first plate 420 includes a proximal end 421 and a distal end 422 opposite from one another, and a mid-longitudinal axis extending through the proximal end 421 and the distal end 422. The first plate 420 also includes a bone contacting surface 429 extending from the proximal end 421 to the distal end 422. The first plate 420 further includes a first link 423 or first pair of links 423 proximate the proximal end 421 of the first plate 420. The first plate 420 also includes a second link 424 or second pair of links 424 proximate the distal end 422 of the first plate 420.

Similar to the first plate 420, the second plate 430 includes a proximal end 431 and a distal end 432 opposite from one another, and a mid-longitudinal axis extending through the proximal end 431 and the distal end 432. The second plate 430 also includes a bone contacting surface 439 extending from the proximal end 431 to the distal end 432. The second plate 430 further includes a third link 433 or third pair of links 433 proximate the proximal end 431 of the second plate 430. The second plate 430 also includes a fourth link 434 or fourth pair of links 434 proximate the distal end 432 of the second plate 430.

The first transverse members 440A and 44B have the first link 423 or first pair of links 423 and the third link 433 or third pair of links 433 rotationally attached thereto. The first transverse members 440A and 440B have openings 441A, 441B extending therethrough, the respective openings 441A, 441B including threads 442A, 442B therein.

The second transverse members 450A and 450B have the second link 424 or second pair of links 424 in the fourth link 434 or fourth pair of links 434 rotationally attached thereto. The second transverse members 450A and 450B have openings 451A, 451B extending at least partially therein.

The side-by-side screws 460A, 460B include threads 363A, 363B, respectively, along a majority of the length thereof. The threads 363A, 363B correspond to mate with the threads 442A, 442B within the respective openings 441A, 441B of the first transverse members 440A, 440B. The screws 460A, 460B also include threadless leading portions 461A, 461B sized to fit, and rotate freely, within the openings 451A, 451B of the second transverse members 450A, 450B. The screws 460A, 460B also include openings 462A, 462B in the trailing ends configured to receive an expansion tool (not shown) therein. The openings may be shaped to accept a hex key, hexalobular key, or any other suitable driver configuration.

As shown in FIGS. 34-38, the unexpanded configuration of the expandable spinal implant 410 includes the bone contacting surfaces 429, 439 of the first plate 420 and the second plate 430 aligned in a parallel orientation. The distal end 422 of first plate 420 and the distal end 432 of second plate 430 are both tapered, or convex, to facilitate insertion of the expandable spinal implant 410 into the disc space between the two adjacent vertebrae. The central longitudinal axes of both of the links or pairs of links 433, 434 form acute angles with the mid-longitudinal axis of the second plate 430.

The expandable spinal implant 410 is affixed to an insertion tool (not shown) which may closely match either the interior surfaces or exterior surfaces of the proximal ends 421 and 431 of the first and second plates 420 and 430. In addition, the proximal ends 421 and 431 of the first and second plates 420 and 430 may also include notches to cooperate with a detent mechanism located on the distal end of the inserter, thereby preventing relative motion between the expandable spinal implant 410 and the inserter until the expandable spinal implant 410 has been positioned correctly within the disc space and the detent is released via a control located on the proximal end of the inserter.

After the expandable spinal implant 410 is properly placed into the disc space, the expansion tools are inserted into the openings 462A, 462B of the respective screws 460A, 460B and the expansion tools are rotated to advance the screws 460A, 460B through the openings 441A, 441B of the first transverse member 440. As the screws 460A, 460B advances through the openings 441A, 441B of the first transverse members 440A, 440B, threadless leading portions 461A, 461B rotate freely within the openings 451A, 451B of the second transverse members 450A, 450B, and the shoulder where leading portions 461A, 461B abut the threaded portion of the screws 460A, 460B applies a force against the second transverse members 450A, 450B. The opposing forces generated by the screw threads 463A, 463B against the opening threads 442A, 442B and the shoulder against second transverse members 450A, 450B causes the first transverse members 440A, 440B to move toward the proximal end 431 of the second plate 430 and the second transverse members 450A, 450B to move toward the distal ends 422, 432 of the first and second plates 420, 430. The first transverse members 440A, 440B are in a fixed translational relationship with the first plate 420, i.e. first transverse members 440A, 440B may rotate within the first pair of openings but the first transverse members cannot translate relative to the first plate. However, because the second transverse members 450A, 450B are free to translate within the second pair of openings, the separation of the first and second transverse members 440A, 440B, 450A, 450B causes the first plate 420 to translate toward the proximal end 431 the second plate 430. The movement of the transverse members 440A, 440B, 450A, 450B causes the rotationally attached links or pairs of rotationally attached links 433, 434 to rotate about the axes of rotation located proximate the bone contact surface of the second plate. The rotation of the two links or pairs of links 433, 434 preferably causes the links or pairs of links to plastically deform, thereby enabling the links or pairs of links to maintain their new positions in the expanded configuration.

Figure 40:
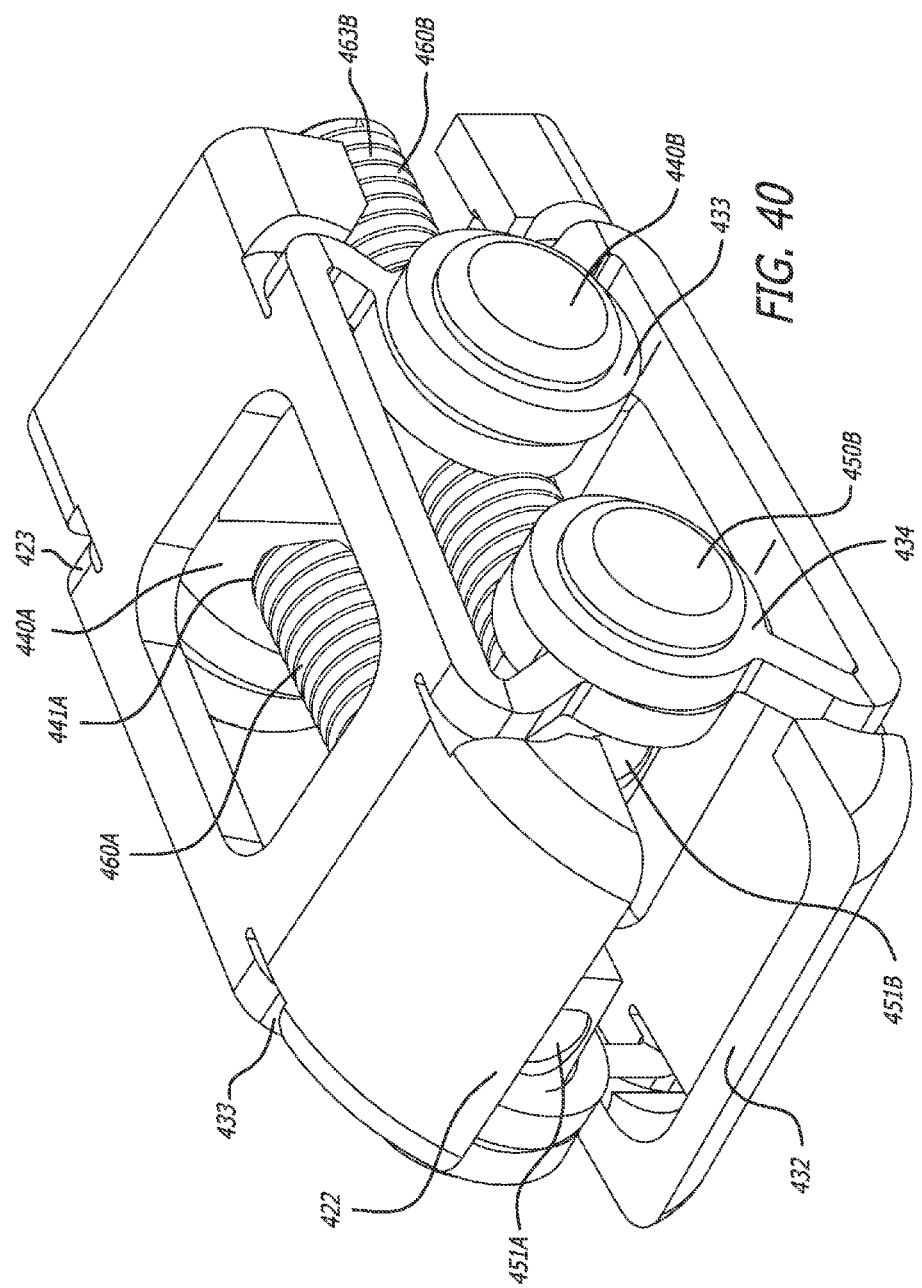
FIG. 40 is a front perspective view of the expandable spinal implant of FIG. 34 in the expanded configuration.
Figure 41:
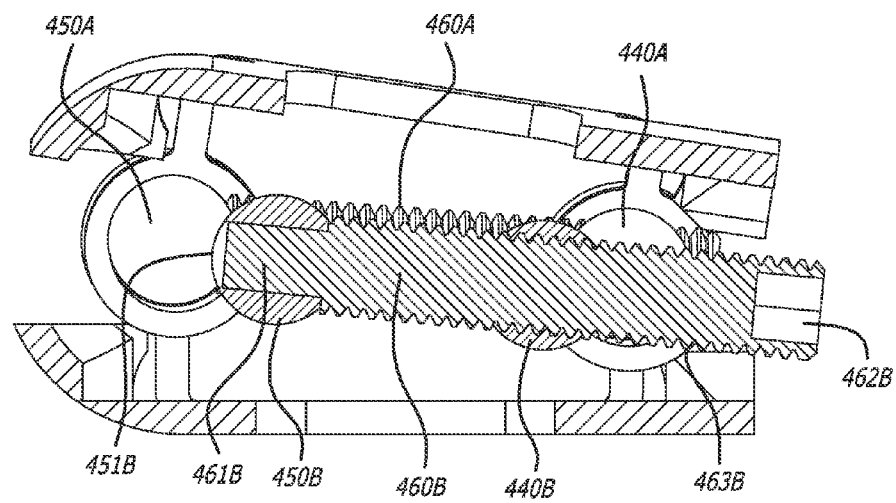
FIG. 41 is a side cross-sectional view along Line 41-41 of FIG. 39 showing the expandable spinal implant of FIG. 34 in the expanded configuration.
Figure 42:
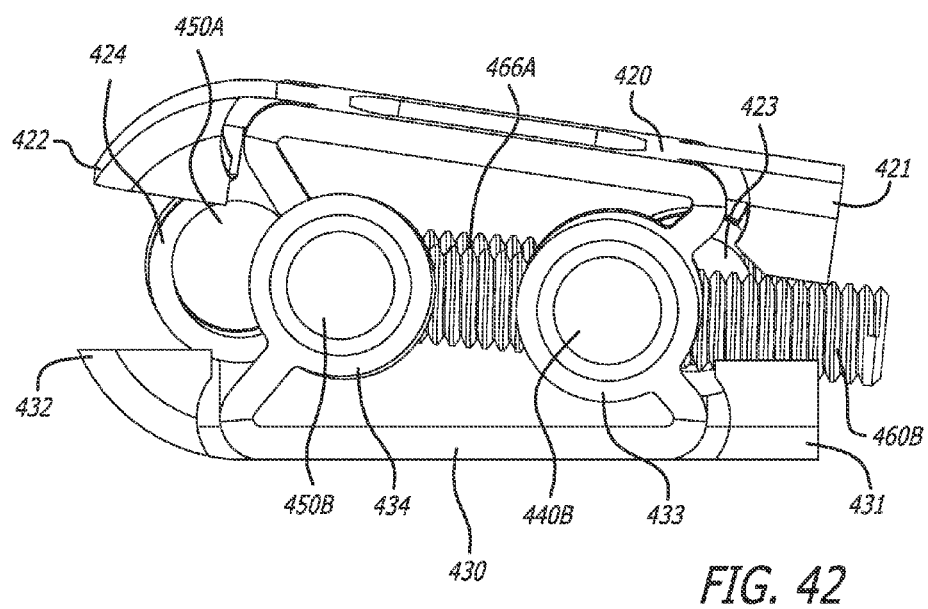
FIG. 42 is a side view of the expandable spinal implant of FIG. 34 in the expanded configuration.

As shown in FIGS. 40-42, when the expandable spinal implant 410 is fully expanded, the links or pairs of links 433, 434 are approximately perpendicular to the bone contacting surface 439 of the second plate 430. This is the preferred arrangement so as to provide optimal load transfer through the links or pairs of links 433, 434 prior to complete fusion of the joint. In order to prevent accidental overexpansion of the expandable spinal implant 410, the expansion tools (not shown) that are utilized to rotate the screws 460A, 460B may include shrouds that surrounds the trailing ends of screws 460A, 460B while the tip of the expansion tools are inserted into the respective openings 462A, 462B. The shrouds should extend approximately as long as the tip of the expansion tool. As such, as the trailing ends of the screws 460A, 460B advances into the openings 441A, 441B of the first transverse members 440A, 440B, the shrouds will encounter the first transverse members 440A, 440B, and therefore, be prevented from further advancement. When the expandable spinal implant 410 has achieved full expansion, interference between the shrouds and the first transverse members will prevent the tips of the expansion tools from being able reach into the openings 462A, 462B, thereby preventing further rotation/advancement of the screws 460A and 460B. In addition, the first transverse members 440A, 440B may include a groove surrounding the openings to cooperate with the shrouds as they contact the first transverse members to prevent the expansion tools from slipping laterally as the tips of the expansion tools are separated from the openings 462A, 462B.

Figure 39:
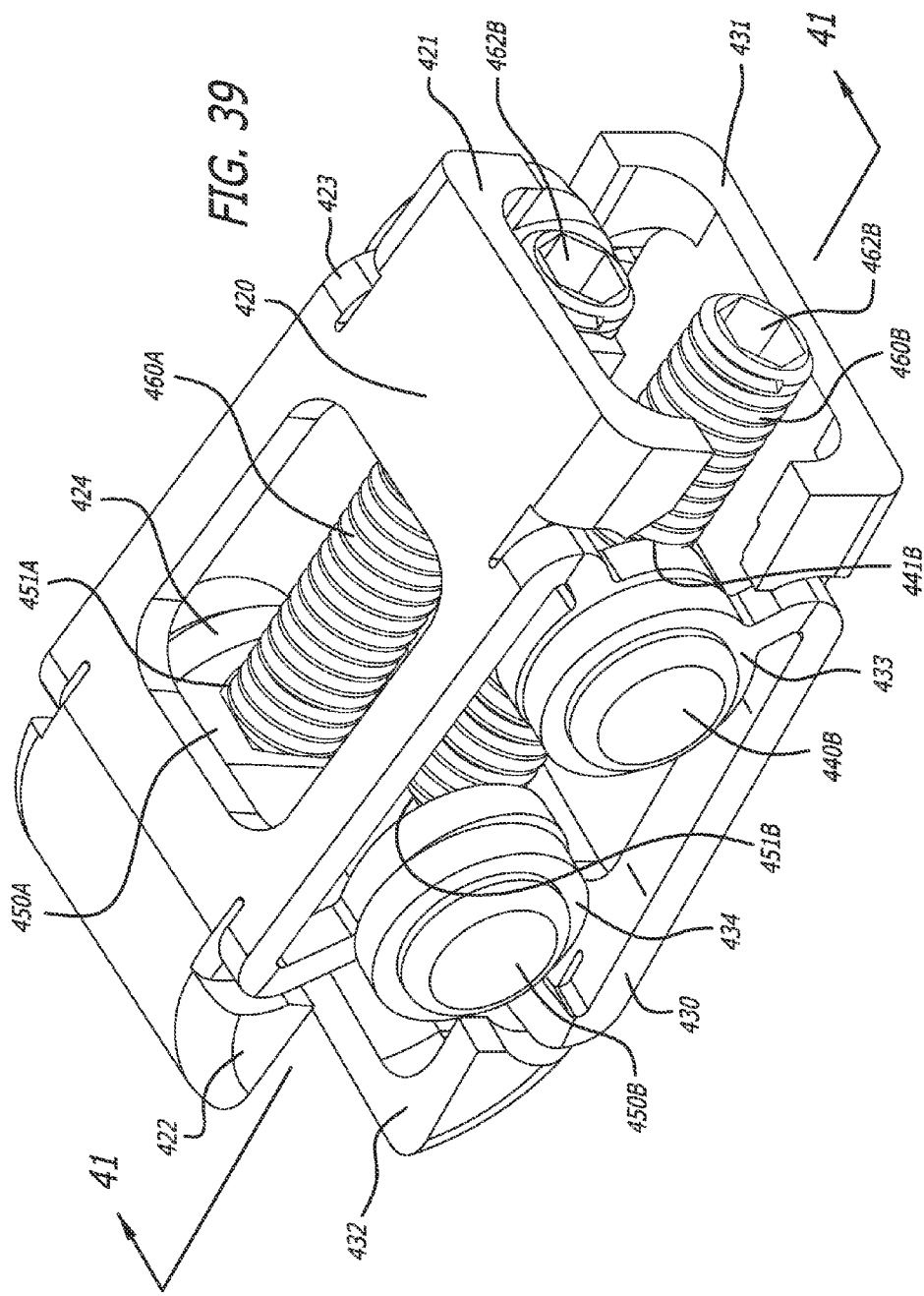
FIG. 39 is a rear perspective view of the expandable spinal implant of FIG. 34 in the expanded configuration.
Figure 43:
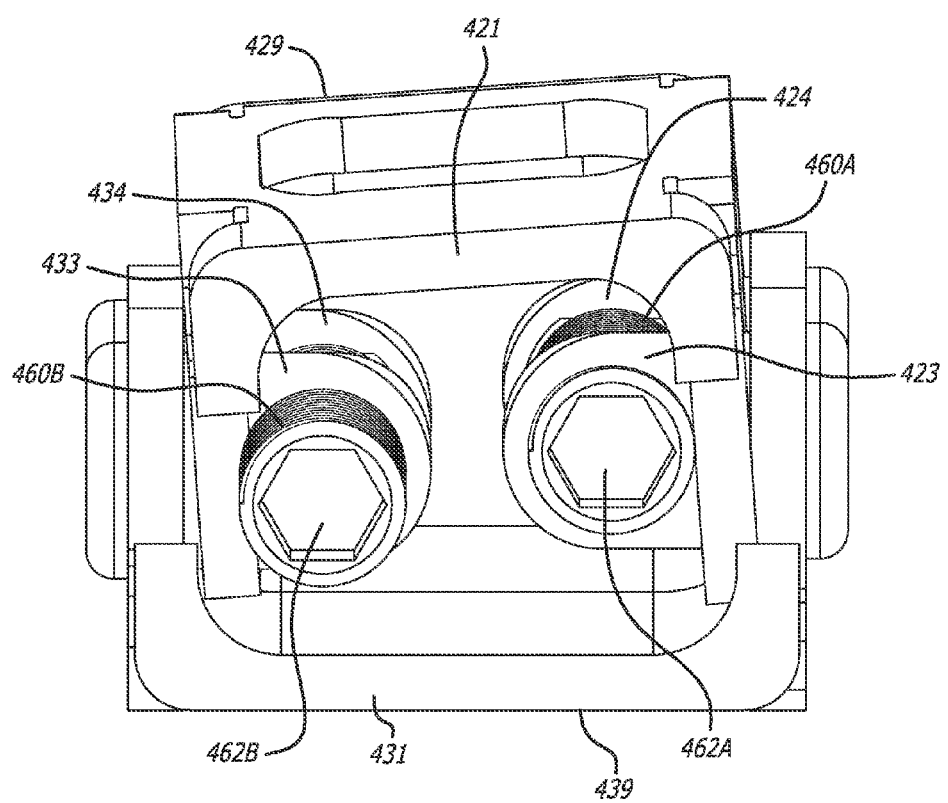
FIG. 43 is a rear view of the expandable spinal implant of FIG. 34 in a partially-expanded configuration.
Figure 44:
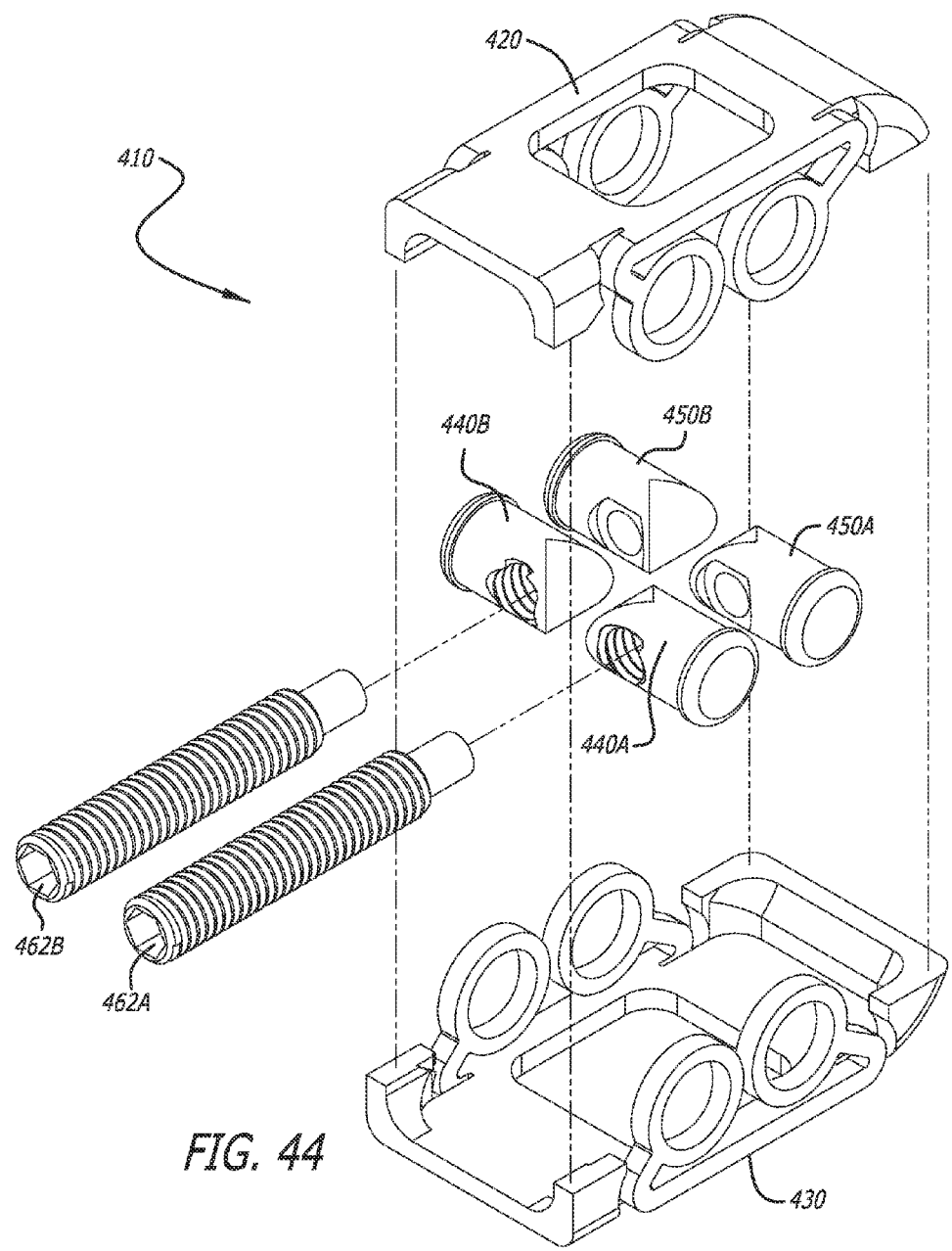
FIG. 44 is an exploded parts view of the expandable spinal implant of FIG. 34.

As shown in FIGS. 39 and 43, the screws 460A and 460B may be advanced unevenly in order to create a lordic, tilting implant 410.

In addition to being useful for restoring lordosis or kyphosis, the relative translation of the first and second plates 420, 430 may be useful for spondylosthesis reduction.

It may be desirable to further modify the expandable implant 410 such that the bone contacting surfaces 429, 439 are convex or biconvex, in order to mimic the shapes of the endplates of the adjacent vertebrae. In addition, it may be desirable to add bone engaging projections to the bone contacting surfaces 429, 439, in order to prevent unwanted migration of the expandable spinal implant 410 prior to achieving the desired fusion.

The expandable spinal implant 410 is preferably made of a machined or milled metal, including but not limited to titanium, stainless steel and/or nickel-titanium shape memory materials (trade name NITINOL) suitable for implantation within the body. Alternatively the expandable spinal implant 410 can be made from a biocompatible polymer (such as PEEK, for example). In some such embodiments, the biocompatible polymer may be provided with a titanium coating at selected areas (such as areas in contact with vertebral endplates), and/or radiopaque markers to establish the position and/or orientation of the implant under radiographic observation. However, the expandable spinal implant 410 may be constructed of any material suitable for implantation or a combination of those materials.

After insertion and expansion of the expandable spinal implant 410, it may be desirable to fill the space between the first and second plates 420, 430 with a fusion promoting substance to facilitate its use as a spinal fusion cage.

The various elements of the different embodiments may be used interchangeably without deviating from the present invention. Moreover, other embodiments of the invention will be apparent to those skilled in the art from consideration of the specification and practice of the invention disclosed herein. It is intended that the specification and examples be considered as exemplary only, with a true scope and spirit of the invention being indicated by the following dams.

What is claimed is:

1. An expandable spinal implant for insertion into a disc space between two adjacent vertebrae, the implant comprising:
   a first plate having a proximal end, an opposite distal end, a bone contacting surface, a mid-longitudinal axis extending through the proximal end and the distal end, one of a first link and a first pair of links extending away from the bone contacting surface at an acute angle to a plane including the mid-longitudinal axis proximate the proximal end, and one of a second link and a second pair of links extending away from the bone contacting surface at an acute angle to the plane including the mid-longitudinal axis proximal the distal end;
   a second plate having a proximal end, an opposite distal end, a bone contacting surface, a mid-longitudinal axis extending through the proximal end and the distal end, one of a third link and a third pair of links extending away from the bone contacting surface at an acute angle to a plane including the mid-longitudinal axis proximate the proximal end, and one of a fourth link and a fourth pair of links extending away from the bone contacting surface at an acute angle to the plane including the mid-longitudinal axis proximal the distal end;
   a first transverse member located between the bone contacting surfaces of the first and second plates substantially transverse to the mid-longitudinal axis, the first transverse member having the one of the first and third links and the first and third pairs of links rotationally attached thereto, the first transverse member including a threaded opening extending therethrough, the threaded opening being substantially parallel to the mid-longitudinal axis;
   a second transverse member located between the bone contacting surfaces of the first and second plates substantially transverse to the mid-longitudinal axis having the one of the second and fourth links and the second and fourth pairs of links rotationally attached thereto, the second transverse member including an opening extending at least partially therein, the opening being substantially parallel to the mid-longitudinal axis; and
   a screw including a leading portion and an opposite trailing portion, the screw including threads that mate with the threads of at least the threaded opening of the first transverse member, the leading portion of the screw being sized to fit at least in part within the opening of the second transverse member;
   wherein the screw is configured to be advanced through the opening in the first transverse member and into the opening in the second transverse member, and continued advancement forces separation of the first and second transverse members away from each other to cause plastic deformation of the one of four links and four pairs of links until the one of the first and second links and first and second pairs of links form approximately right angles with the plane including the mid-longitudinal axis of the first plate and the third and fourth pairs of links form approximately right angles with the plane including the mid-longitudinal axis of the second plate, the deformation of the one of four links and four pairs of links causing the first and second plate to separate from one another to transition from a first unexpanded configuration to a second expanded configuration.

2. The expandable spinal implant of claim 1, further including at least one opening in the first plate and at least one opening in the second plate configured for bone growth therethrough between the two adjacent vertebrae.

3. The expandable spinal implant of claim 1, wherein the distal ends of the first and second plates are tapered to facilitate insertion of the expandable spinal implant into the disc space.

4. The expandable spinal implant of claim 1, wherein the proximal ends of the first and second plates are shaped to cooperatively engage an insertion tool to facilitate insertion of the expandable spinal implant into the disc space.

5. The expandable spinal implant of claim 1, wherein the trailing portion of the screw includes an opening configured to receive an expansion tool therein to facilitate rotation of the screw.

6. The expandable spinal implant of claim 1, wherein lengths of the one of first and second links and the first and second pairs of links are different lengths, causing the bone contacting surfaces of the first and second plates to be angled relative to one another in the expanded configuration.

7. A method of implanting an expandable spinal implant into a disc space between two adjacent vertebrae, the method comprising:
   utilizing the expandable spinal implant comprising:
      a first plate having a bone contacting surface and one of first and second links and first and second pairs of links extending away from the bone contacting surface of the first plate;
      a second plate having a bone contacting surface and one of third and fourth links and third and fourth pairs of links extending away from the bone contacting surface of the second plate;
      a first transverse member rotationally attached to the one of the first and third links and the first and third pairs of links, the first transverse member including a threaded opening extending therethrough;
      a second transverse member rotationally attached to the one of the second and fourth links and the second and fourth pairs of links, the second transverse member including an opening extending at least partially therein; and
      a screw threaded through the threaded opening in the first transverse member, the screw including a non-threaded leading end inserted into the opening in the second transverse member;
   inserting the expandable spinal implant into the disc space between two adjacent vertebrae; and
   rotating the screw, wherein rotating the screw causes the transverse members to separate, which causes rotational deformation of the one of the four links and the four pairs of links and separation of the first and second plates.

8. The method of claim 7, further comprising inserting bone growth material between the first and second plate after the implant is inserted in the disc space.

9. The method of claim 7, wherein the inserting the expandable spinal implant includes engaging proximal ends of the first and second plates with an inserter configured to cooperatively engage therewith.

10. The method of claim 7, wherein the rotating the screw includes inserting an expansion tool into a recess in a trailing end of the screw.

* * * * *

UNITED STATES PATENT AND TRADEMARK OFFICE
CERTIFICATE OF CORRECTION

Page 1 of 2

PATENT NO. : 9,713,536 B2
APPLICATION NO. : 14/824965
DATED : July 25, 2017
INVENTOR(S) : Foley et al.

It is certified that error appears in the above-identified patent and that said Letters Patent is hereby corrected as shown below:

In the Specification

In Column 5, Line 1, delete "unexpended" and insert -- unexpanded --, therefor.

In Column 5, Line 61, delete "Iinks" and insert -- links --, therefor.

In Column 7, Line 19, delete "reach" and insert -- to reach --, therefor.

In Column 7, Line 66, delete "biocornpaiible" and insert -- biocompatible --, therefor.

In Column 9, Line 59, delete "trang" and insert -- trailing --, therefor.

In Column 10, Line 2, delete "reach" and insert -- to reach --, therefor.

In Column 11, Line 22, delete "OLE" and insert -- OLIF --, therefor.

In Column 12, Line 16, delete "trading" and insert -- trailing --, therefor.

In Column 12, Line 23, delete "reach" and insert -- to reach --, therefor.

In Column 12, Line 59, delete "members 340," and insert -- member 340, --, therefor.

In Column 13, Line 35, delete "trading" and insert -- trailing --, therefor.

In Column 15, Line 24, delete "screws screw" and insert -- screws --, therefor.

In Column 17, Line 19, delete "reach" and insert -- to reach --, therefor.

Signed and Sealed this
Sixth Day of February, 2018

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,713,536 B2

In Column 17, Line 28, delete "lordic," and insert -- lordotic, --, therefor.

In Column 17, Line 67, delete "dams." and insert -- claims. --, therefor.